(12) United States Patent
Gu et al.

(10) Patent No.: US 7,425,538 B2
(45) Date of Patent: Sep. 16, 2008

(54) HAUSP-P53 INTERACTION AND USES THEREOF

(75) Inventors: Wei Gu, New York, NY (US); Muyang Li, New York, NY (US)

(73) Assignee: The trustess of Columbia University in the City of New York, New York, NY (US)

( * ) Notice: Subject to any disclaimer, the term of this patent is extended or adjusted under 35 U.S.C. 154(b) by 174 days.

(21) Appl. No.: 10/113,732

(22) Filed: Mar. 30, 2002

(65) Prior Publication Data

US 2003/0186861 A1   Oct. 2, 2003

(51) Int. Cl.
  *A61K 38/00* (2006.01)
  *G01N 33/53* (2006.01)
(52) U.S. Cl. .............................. 514/12; 435/6; 435/7.1; 435/7.23
(58) Field of Classification Search .................. 435/6, 435/7.1, 7.23
  See application file for complete search history.

(56) References Cited

U.S. PATENT DOCUMENTS 6,083,709 A * 7/2000 Reynolds et al. ........... 435/7.94
  2004/0265931 A1  12/2004 Gu et al.

FOREIGN PATENT DOCUMENTS

WO   WO 01/32696 A2   5/2001
  WO   WO 0132696 A2 *  5/2001

OTHER PUBLICATIONS

Kashuba et al. (FEBS Letters 1997, 419; 181-185).*
Ovaa et al. (PNAS 2004; 101: 2253-2258).*
Muratani et al. (Nat. Cell Bio. 2002; 4: 106-110).*
E. Appella and CW Anderson, *Signaling to p53: Breaking the Post-translational Modification Code*, Pathol. Biol. (Paris) 48:227-45 (Apr. 2000) (abstract only).
Margaret Ashcroft and Karen H. Vousden, *Regulation of p53 Stability*, Oncogene, 18:7637-43 (Dec. 1999) (abstract only).
Margaret Ashcroft et al., *Regulation of p53 Function and Stability by Phophorylation*, Mol. Cell Biol., 19:1751-58 (Mar. 1999).
Margaret Ashcroft et al, *Stress Signals Utilize Multiple Pathways to Stabilize p53*, Mol. Cell Biol., 20:3224-33 (May 2000).
Y. Barak et al., *mdm2 Expression is induced by Wild Type p53 Activity*, EMBO J., 12:461-68 (Feb. 1993) (abstract only).
Christine Blattner et al., *DNA Damage Induced p53 Stabilization: No Indication for an Involvement of p53 Phosphorylation*, Oncogene, 18:1723-32 (Mar. 1999) (abstract only).
Vladimir Botchkarev et al., *p53 is Essential for Chemotherapy-induced Hair Loss*, Cancer Res., 60:5002-06 (Sep. 2000).
Chin Ha Chung and Sung Hee Baek, *Deubiquitinating Enzymes: Their Diversity and Emerging Roles*, Biochem. Biophys. Res. Commun., 266:633-40 (Dec. 1999) (abstract only).
A. D'Andrea and D. Pellman, *Deubiquitinating Enzymes: A New Class of Biological Regulators*, Crit. Rev. Biochem. Mol. Biol., 33(5):337-52 (1998) (abstract only).

L.A. Donehower et al., *Mice Deficient for p53 are Developmentally Normal but Susceptible to Spontaneous Tumors*, Nature, 356:215-21 (Mar. 1992) (abstract only).
Nicolas Dumaz and David W. Meek, *Serine 15 Phosphorylation Stimulates p53 Transactivation but Does Not Directly Influence Interaction with HDM2*, EMBO J., 18:7002-10 (1999).
W.S. el-Deiry et al., *WAF1, A Potential Mediator of p53 Tumor Suppression*, Cell, 75:817-825 (Nov. 1993) (abstract only).
Roger D. Everett et al., *A Novel Ubiquitin-specific Protease is Dynamically Associated with the PML Nuclear Domain and Binds to a Herpesvirus Regulatory Protein*, EMBO J., 16:1519-30 (1997).
D.A. Freedman et al., *Functions of the MDM2 Oncoprotein*, Cell Mol. Life Sci., 55:96-107 (Jan. 1999) (abstract only).
Amato J. Giaccia and Michael B. Kastan, *The Complexity of p53 Modulation: Emerging Patterns from Divergent Signals*, Genes & Dev., 12:2973-83 (1998).
W. Gu et al., *Synergistic Activation of Transcription by CBP and p53*, Nature, 387:819-23 (Jun. 1997) (abstract only).
Y. Haupt et al, *Mdm2 Promotes the Rapid Degradation of p53*, Nature, 387:296-99 (May 1997) (abstract only).
Avram Hershko et al., *The Ubiquitin System*, Nat. Med., 6:1073-81 (Oct. 2000).
M. Hollstein et al., *Database of p53 Gene Somatic Mutations in Human Tumors and Cell Lines*, Nucleic Acids Res., 22:3551-55 (Sep. 1994) (abstract only).
M. Hollenstein et al., *New Approaches to Understanding p53 Gene Tumor Mutation Spectra*, Mutat. Res., 431:199-209 (Dec. 1999) (abstract only).
Reiko Honda et al., *Oncoprotein MDM2 is a Ubiquitin Ligase E3 for Tumor Suppressor p53*, FEBS Letters, 420:25-27 (1997).
M. H. Kabbutat et al., *Regulation of p53 Stability by Mdm2*, Nature, 387:299-303 (May 1997) (abstract only).

(Continued)

*Primary Examiner*—Brandon J Fetterolf
(74) *Attorney, Agent, or Firm*—Wilmer Cutler Pickering Hale and Dorr LLP

(57) ABSTRACT

The present invention provides methods for determining whether a subject has neoplasia, methods for assessing the efficacy of therapy to treat neoplasia in a subject, methods for assessing the prognosis of a subject who has neoplasia, and methods for treating neoplasia in a subject in need of treatment. The present invention further provides a kit for use in detecting neoplasia. Additionally, the present invention provides a pharmaceutical composition, comprising a modulator of HAUSP expression or a HAUSP protein and a pharmaceutically acceptable carrier. Also provided is a method for deubiquitinating p53 in a cell. The present invention is further directed to a method for identifying an agent that is reactive with p53, and the agent identified by this method. Furthermore, the present invention provides a method for treating a p53-associated condition in a subject in need of treatment. The present invention is also directed to a complex comprising p53 and HAUSP, and a mutant protein comprising the HAUSP amino acid sequence, in which Ser is substituted for Cys at amino acid residue 223. Finally, the present invention provides a transgenic non-human animal whose genome comprises a disruption in its endogenous HAUSP gene.

6 Claims, 10 Drawing Sheets

OTHER PUBLICATIONS

M. B. Kastan et al., *A Mammalian Cell Cycle Checkpoint Pathway Utilizing p53 and GADD45 is Defective in Ataxia-telangiectasia*, Cell, 71:587-97 (Nov. 1992) (abstract only).

Daniel Kornitzer and Aaron Ciechanover, *Modes of Regulation of Ubiquitin-mediated Protein Degradation*, J. Cell. Phys., 182:1-11 (2000) (abstract only).

D. P. Lane, *Cancer. p53, guardian of the genome*, Nature, 358:15-16 (Jul. 1992) (abstract only).

J. D. Laney and M. Hochstrasser, *Substrate Targeting in the Ubiquitin System*, Cell, 97:427-30 (May 1999) (no abstract avail).

A.J. Levine, p53, *The Cellular Gatekeeper for Growth and Division*, Cell 88:323-31 (Feb. 1997) (no abstract available).

J. Luo et al., *Deacetylation of p53 Modulates its Effect on Cell Growth and Apoptosis*, Nature, 408:377-81 (Nov. 2000) (abstract only).

J. Luo et al., *Negative Control of p53 by Sir2a Promotes Cell Survival under Stress*, Cell, 107:137-48 (Oct. 2001) (abstract only).

K. Nakano and K.H. Vousden, *PUMA, A Novel Proapoptic Gene, Is Induced by p53*, Molecular Cell, 7:683-94 (Mar. 2001) (abstract only).

E. Oda et al., *Noxa, a BH3-only Member of the Bcl-2 Family and Candidate Mediator of p53-induced Apoptosis*, Science, 288:1053-58 (May 2000) (abstract only).

K. Oda et al., *p53AIP1, A Potential Mediator of p53-dependent Apoptosis, and its Regulation by Ser-46-phophorylated p53*, Cell, 102:849-62 (Sep. 2000) (abstract only).

K. Okamoto and D. Beach, *Cyclin G is a Transcriptional Target of the p53 Tumor Suppressor Protein*, EMBO J., 13:4816-22 (Oct. 1994) (abstract only).

Moshe Oren, *Regulation of the p53 Tumor Suppressor Protein*, J. Biol. Chem., 274, 36031-034 (Dec. 1999).

Carol Prives and Peter A. Hall, *The p53 Pathway*, J. Pathol., 187:112-26 (1999) (abstract only).

Rodriguez et al., *Multiple C-Terminal Lysine Residues Target p53 for Ubiquitin-Proteasome-mediated Degradation*, Mol. Cell. Biol., 20:8458-67 (Nov. 2000).

M. Scheffner et al., *The HPV-16 E6 and E6-AP Complex Functions as a Ubiquitin-protein Ligase in the Ubiquitination of p53*, Cell, 75:495-505 (Nov. 1993) (abstract only).

Scott E. Seavey et al., *The E7 Oncoprotein of Human Papillomavirus Type 16 Stabilizes p53 Through a Mechanism Independent of p19$^{ARF}$*, J. Virol., 73:7590-98 (Sep. 1999).

C.J. Sherr and J. D. Weber, *The ARF/p53 Pathway*, curr. Opin. Genet. Dev., 10:94-99 (Feb. 2000) (abstract only).

S.Y. Shieh et al., *DNA Damage-induced Phosphorylation of p53 Alleviates Inhibition by MDM2*, Cell, 91:325-34 (Oct. 1997) (abstract only).

Slingerland and Pagano, *Regulation of the Cdk Inhibitor p27 and its Deregulation in Cancer*, J. Cell Physi., 183:10-17 (2000) (abstract only).

Dawn Tolbert et al., *p19$^{ARF}$ is Dispensable for Oncogenic Stress-induced p53-mediated Apoptosis and Tumor Suppression* In Vivo, Mol. Cell Biol., 22:370-77 (Jan. 2002).

B. Vogelstein et al., *Surfing the p53-Network*, Nature, 408:307-10 (Nov. 2000) (no abstract avail.).

Keith D. Wilkinson, *Ubiquitination and Deubiquitination: Targeting of Proteins for Degradation by the Proteasome*, Semin. Cell Dev. Biol., 11:141-48 (Jun. 2000) (abstract only).

X. Wu et al, *The p53-mdm-2 Autoregulatory Feedback Loop*, Genes Dev., 7:1126-32 (Jul. 1993) (abstract only).

J. Yu et al., *PUMA Induces the Rapid Apoptosis of Colorectal Cancer Cells*, Molecular Cell, 7:673-82 (Mar. 2001) (abstract only).

Cummins et al., Disruption of HAUSP gene stabilizes p53. Nature 428:1-2 (2004).

Kashuba, V.I., et al., Notl linking/jumping clones of human chromosome 3:mapping of the TFRC, RAB7 and HAUSP genes to regions rearranged in leukemia and deleted in solid tumors. FEBS Letters 419 (1997) 181-185.

* cited by examiner a
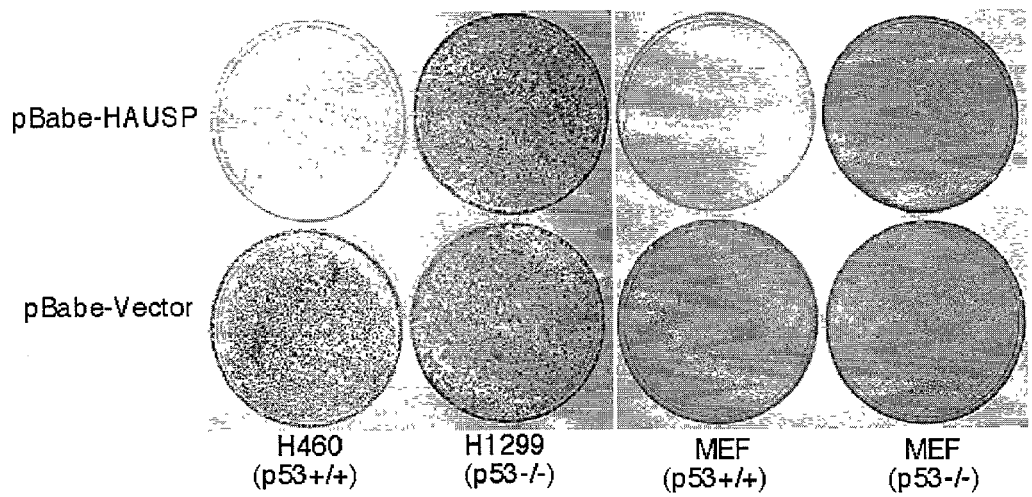
b
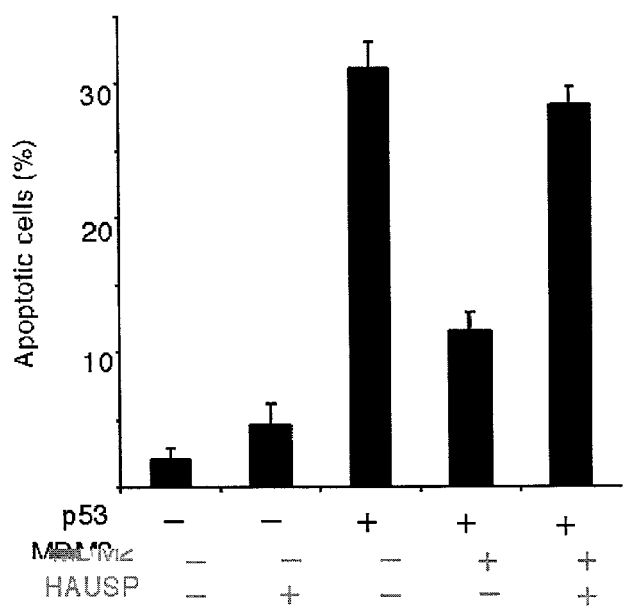
Fig. 3

```
  1 mnhqqqqqqq kageqqlsep edmemeagdt ddppritqnp vingnvalsd ghntaeedme
 61 ddtswrseat fqftverfsr lsesvlsppc fvrnlpwkim vmprfypdrp hqksvgfflq
121 cnaesdstsw schaqavlki inyrddeksf srrishlffh kendwgfsnf mawsevtdpe
181 kgfidddkvt fevfvqadap hgvawdskkh tgyvglknqg atcymnsllq tlfftnqlrk
241 avymmptegd dssksvplal qrvfyelqhs dkpvgtkklt ksfgwetlds fmqhdvqelc
301 rvlldnvenk mkgtcvegti pklfrgkmvs yiqckevdyr sdrredyydi qlsikgkkni
361 fesfvdyvav eqldgdnkyd agehglqeae kgvkfltlpp vlhlqlmrfm ydpqtdqnik
421 indrfefpeq lpldeflqkt dpkdpanyil havlvhsgdn hgghyvvyln pkgdgkwckf
481 dddvvsrctk eeaiehnygg hdddlsvrhc tnaymlvyir esklsevlqa vtdhdipqql
541 verlqeekri eaqkrkerqe ahlymqvqiv aedqfcghqg ndmydeekvk ytvfkvlkns
601 slaefvqsls qtmgfpqdqi rlwpmqarsn gtkrpamldn eadgnktmie lsdnenpwti
661 fletvdpela asgatlpkfd kdhdvmlflk mydpktrsln ycghiytpis ckirdllpvm
721 cdragfiqdt slilyeevkp nlteriqdyd vsldkaldel mdgdiivfqk ddpendnsel
781 ptakeyfrdl yhrvdvifcd ktipndpgfv vtlsnrmnyf qvaktvaqrl ntdpmllqff
841 ksqgyrdgpg nplrhnyegt lrdllqffkp rqpkklyyqq lkmkitdfen rrsfkciwln
901 sqfreeeitl ypdkhgcvrd lleeckkave lgekasgklr lleivsykii gvhqedelle
961 clspatsrtf rieeipldqv didkenemlv tvahfhkevf gtfgipfllr ihqgehfrev
1021 mkriqslldi qekefekfkf aivmtgrhqy inedeyevnl kdfepqpgnm shprpwlgld
1081 hfnkapkrsr ytylekaiki hn
```

Fig. 6

```
   1 gtacgtgcgc gtctccctgc cgccgccgcc gcccgccgcg ggccgccccg gggccgccgt
  61 cgccgacgac gcgcgggagg aggaggagga ggccgccccg ccgccgccgc cgccgccgcc
 121 gccccggctc gccgccgccc gcccgccggg ctcgcagccc cggcccccgg ccgcaggcga
 181 ggcccaggcc gcggccgaca tgaaccacca gcagcagcag cagcagcaga aagcgggcga
 241 gcagcagttg agcgagcccg aggacatgga gatggaagcg ggagatacag atgacccacc
 301 aagaattact cagaaccctg tgatcaatgg gaatgtggcc ctgagtgatg acacaacac
 361 cgcggaggag gacatggagg atgacaccag ttggcgctcc gaggcaacct ttcagttcac
 421 tgtggagcgc ttcagcagac tgagtgagtc ggtccttagc cctccgtgtt ttgtgcgaaa
 481 tctgccatgg aagattatgg tgatgccacg cttttatcca gacagaccac accaaaaaag
 541 cgtaggattc tttctccagt gcaatgctga atctgattcc acgtcatggt cttgccatgc
 601 acaagcagtg ctgaagataa taaattacag agatgatgaa aagtcgttca gtcgtcgtat
 661 tagtcatttg ttcttccata agaaaatga ttggggatttt tccaatttta tggcctggag
 721 tgaagtgacc gatcctgaga aaggatttat agatgatgac aaagttacct ttgaagtctt
 781 tgtacaggcg gatgctcccc atggagttgc gtgggattca agaagcaca caggctacgt
 841 cggcttaaag aatcagggag cgacttgtta catgaacagc ctgctacaga cgttatttt
 901 cacgaatcag ctacgaaagg ctgtgtacat gatgccaacc gaggggatg attcgtctaa
 961 aagcgtccct ttagcattac aaagagtgtt ctatgaatta cagcatagtg ataaacctgt
1021 aggaacaaaa aagttaacaa agtcatttgg gtgggaaaact ttagatagct tcatgcaaca
1081 tgatgttcag gagctttgtc gagtgttgct cgataatgtg gaaaataaga tgaaaggcac
1141 ctgtgtagag ggcaccatac ccaaattatt ccgcggcaaa atggtgtcct atatccagtg
1201 taaagaagta gactatcggt ctgatagaag agaagattat tatgatatcc agctaagtat
1261 caaaggaaag aaaaatatat ttgaatcatt tgtggattat gtggcagtag aacagctcga
1321 tgggggacaat aaatacgacg ctggggaaca tggcttacag gaagcagaga aaggtgtgaa
1381 attcctaaca ttgccaccag tgttacatct acaactgatg agatttatgt atgaccctca
1441 gacggaccaa aatatcaaga tcaatgatag gtttgaattc ccagagcagt taccacttga
1501 tgaatttttg caaaaaacag atcctaagga ccctgcaaat tatattcttc atgcagtcct
1561 ggttcatagt ggagataatc atggtggaca ttatgtggtt tatctaaacc ccaaagggga
1621 tggcaaatgg tgtaaatttg atgacgacgt ggtgtcaagg tgtactaaag aggaagcaat
1681 tgagcacaat tatgggggtc acgatgacga cctgtctgtt cgacactgca ctaatgctta
1741 catgttagtc tacatcaggg aatcaaaact gagtgaagtt ttacaggcgg tcaccgacca
1801 tgatattcct cagcagttgg tggagcgatt acaagaagag aaaaggatcg aggctcagaa
1861 gcggaaggag cggcaggaag cccatctcta tgcaagtg cagatagtcg cagaggacca
1921 gttttgtggc caccaaggga atgacatgta cgatgaagaa aaagtgaaat acactgtgtt
1981 caaagtattg aagaactcct cgcttgctga gtttgttcag agcctctctc agaccatggg
2041 atttccacaa gatcaaattc gattgtggcc catgcaagca aggagtaatg gaacaaaacg
2101 accagcaatg ttagataatg aagccgacgg caataaaaca atgattgagc tcagtgataa
2161 tgaaaaccct tggacaatat tcctggaaac agttgatccc gagctggctg ctagtggagc
2221 gaccttaccc aagtttgata agatcatga tgtaatgtta ttttgaagaa tgtatgatcc
2281 caaaacgcgg agcttgaatt actgtgggca tatctacaca ccaatatcct gtaaaatacg
```

Fig. 7

```
2341 tgacttgctc ccagttatgt gtgacagagc aggatttatt caagatacta gccttatcct
2401 ctatgaggaa gttaaaccga atttaacaga gagaattcag gactatgacg tgtctcttga
2461 taaagcccct gatgaactaa tggatggtga catcatagta tttcagaagg atgaccctga
2521 aaatgataac agtgaattac ccaccgcaaa ggagtatttc cgagatctct accaccgcgt
2581 tgatgtcatt ttctgtgata aaacaatccc taatgatcct ggatttgtgg ttacgttatc
2641 aaatagaatg aattattttc aggttgcaaa gacagttgca cagaggctca acacagatcc
2701 aatgttgctg cagttttca agtctcaagg ttatagggat ggcccaggta atcctcttag
2761 acataattat gaaggtactt taagagatct tctacagttc ttcaagccta gacaacctaa
2821 gaaactttac tatcagcagc ttaagatgaa aatcacagac tttgagaaca ggcgaagttt
2881 taatgtata tggttaaaca gccaatttag ggaagaggaa ataacactat atccagacaa
2941 gcatgggtgt gtccgggacc tgttagaaga atgtaaaaag gccgtggagc ttggggagaa
3001 agcatcaggg aaacttaggc tgctagaaat tgtaagctac aaaatcattg gtgttcatca
3061 agaagatgaa ctattagaat gtttatctcc tgcaacgagc cggacgtttc gaatagagga
3121 aatccctttg gaccaggtgg acatagacaa agagaatgag atgcttgtca cagtggcgca
3181 tttccacaaa gaggtcttcg gaacgttcgg aatcccgttt ttgctgagga tacaccaggg
3241 cgagcatttt cgagaagtga tgaagcgaat ccagagcctg ctggacatcc aggagaagga
3301 gtttgagaag tttaaatttg caattgtaat gacgggccga caccagtaca taaatgaaga
3361 cgagtatgaa gtaaatttga aagactttga gccacagccc ggtaatatgt ctcatcctcg
3421 gccttggcta gggctcgacc acttcaacaa agccccaaag aggagtcgct acacttacct
3481 tgaaaaggcc attaaaatcc ataactgatt tccaagctgg tgtgttcaag gcgaggacgg
3541 tgtgtgggtg gcccttaac agcctagaac tttggtgcac gtgccctcta gccgaagtct
3601 tcagcaagag gattcgctgc tggtgttaat tttattttat tgaggctgtt cagtttggct
3661 tctctgtatc tattgactgc ccttttgag caaaatgaag atgtttttat aaagcttgga
3721 tgccaatgag agttatttta tggtaaccac agtgcaaggc aactgtcagc gcaatgggg
3781 agaagaggtt agtggatcgg gggtccctgg ctcaaggtct ctgggctgtc cctagtgggc
3841 acgagtggct cggctgcctt cctggggtcc cgtgcaccag ccctgcagct agcaagtctt
3901 gtgtttaggc tcgtctgacc tatttccttc agttatactt tcaatgacct tttgtgcatc
3961 tgttaaggca aaacagagaa actcacaacc taataaatag cgctcttccc ttcaaaaaaa
4021 aa
```

HAUSP-P53 INTERACTION AND USES THEREOF

STATEMENT OF GOVERNMENT INTEREST

This invention was made with government support under NIH Grant No. RO1-CAS5533. As such, the United States government has certain rights in this invention.

BACKGROUND OF THE INVENTION

Neoplasia is a disease characterized by an abnormal proliferation of cell growth known as a neoplasm. Neoplasms may manifest in the form of a leukemia or a tumor, and may be benign or malignant. Malignant neoplasms, in particular, can result in a serious disease state, which may threaten life. Significant research efforts and resources have been directed toward the elucidation of antineoplastic measures, including chemotherapeutic agents, which are effective in treating patients suffering from neoplasia. Effective antineoplastic agents include those which inhibit or control the rapid proliferation of cells associated with neoplasms, those which effect regression or remission of neoplasms, and those which generally prolong the survival of patients suffering from neoplasia. Successful treatment of malignant neoplasia, or cancer, requires elimination of all malignant cells, whether they are found at the primary site, or have extended to local/regional areas, or have metastasized to other regions of the body. The major therapies for treating neoplasia are surgery and radiotherapy (for local and local/regional neoplasms) and chemotherapy (for systemic sites) (Beers and Berkow (eds.), The Merck Manual of Diagnosis and Therapy, $17^{th}$ ed. (Whitehouse Station, N.J.: Merck Research Laboratories, 1999) 973-74, 976, 986, 988, 991).

Despite the various methods for detecting, diagnosing, and treating cancers, the disease remains prevalent in all segments of society, and is often fatal. Clearly, alternative strategies for detection (including the development of markers that can identify neoplasias at an early stage) and treatment are needed to improve survival in cancer patients. In particular, a better understanding of tumor suppressors, and tumor-suppression pathways, would provide a basis from which novel detection, diagnostic, and treatment regimens may be developed.

The p53 tumor suppressor exerts anti-proliferative effects, including growth arrest, apoptosis, and cell senescence, in response to various types of stress (Levine, A. J., p53, the cellular gatekeeper for growth and division. Cell, 88:323-31, 1997; Giaccia and Kastan, The complexity of p53 modulation: emerging patterns from divergent signals. Genes Dev., 12:2973-83, 1998; Prives and Hall, The p53 pathway. J. Pathol., 187:112-26, 1999; Oren, M., Regulation of the p53 tumor suppressor protein. J. Biol. Chem., 274, 36031-034, 1999; Vogelstein et al., supra). p53 is the most commonly mutated gene in human cancers, with more than 50% of tumors displaying some alteration in p53 (Hollstein et al., New approaches to understanding p53 gene tumor mutation spectra. Mutat. Res., 431:199-209, 1999; Hollstein et al., Database of p53 gene somatic mutations in human tumors and cell lines. Nucleic Acids Res., 22:3551-55, 1994).

Wild-type p53 has been called the guardian of the genome, as it responds to DNA damage or checkpoint failure by either arresting the cell in the $G_1$ phase for damage repair or initiating an apoptotic pathway to eliminate the damaged cell entirely (Lane, D. P., Nature, 358:15-16, 1992; Levine, A. J., supra). p53 is also critical for maintenance of genomic stability, aberrant ploidy, gene amplification, increased recombination, and centrosomal dysregulation—all of which have been observed in cells lacking functional p53 (Donehower et al., Nature, 356:215-21, 1992). These data suggest that abrogation of p53 function is critical in tumorigenesis of cancer. Additionally, numerous studies indicate that inactivation of the p53 pathway is a pivotal event in tumorigenesis of all kinds of human cancers, including breast cancer (Vogelstein et al., Surfing the p53 network. Nature, 408:307-10, 2000). Accumulating evidence further indicates that, in cells that retain wild-type p53, other defects in the p53 pathway play an important role in tumorigenesis (Prives and Hall, supra; Oren, M., supra).

p53 is a short-lived protein whose activity is maintained at low levels in normal cells. The molecular function of p53 that is required for tumor suppression involves the ability of p53 to act as a transcriptional factor in regulating endogenous gene expression. A number of genes which are critically involved in either cell growth arrest or apoptosis have been identified as p53 direct targets, including $p21^{CIP1/WAF1}$, Mdm2, GADD45, Cyclin G, 14-3-3σ, Noxa, p53AIP1, and PUMA (Nakano and Vousden, PUMA, a novel proapoptotic gene, is induced by p53. Molecular Cell, 7:683-94, 2001; Yu et al., PUMA induces the rapid apoptosis of colorectal cancer cells. Molecular Cell, 7:673-82, 2001; Oda et al., Noxa, a BH3-only member of the Bcl-2 family and candidate mediator of p53-induced apoptosis. Science, 288:1053-58, 2000a; Oda et al., p53AIP1, a potential mediator of p53-dependent apoptosis, and its regulation by Ser-46-phosphorylated p53. Cell, 102:849-62, 2000b; el-Deiry et al., WAF1, a potential mediator of p53 tumor suppression. Cell, 75:817-825, 1993; Wu et al., The p53-mdm-2 autoregulatory feedback loop. Genes Dev., 7:1126-32, 1993; Barak et al., mdm2 expression is induced by wild type p53 activity. EMBO J., 12:461-68, 1993; Kastan et al., A mammalian cell cycle checkpoint pathway utilizing p53 and GADD45 is defective in ataxia-telangiectasia. Cell, 71:587-97, 1992; Okamoto and Beach, Cyclin G is a transcriptional target of the p53 tumor suppressor protein. EMBO J., 13:48 16-22, 1994). Furthermore, tight regulation of p53 itself is essential for its effect on tumorigenesis and the maintenance of normal cell growth.

Numerous studies imply the existence of multiple pathways involved in p53 stabilization (Shieh et al., DNA damage-induced phosphorylation of p53 alleviates inhibition MDM2. Cell, 91:325-34, 1997; Appella and Anderson, Signaling to p53: breaking the posttranslational modification code. Pathol. Biol. (Paris), 48:227-45, 2000; Ashcroft et al., Regulation of p53 function and stability by phosphorylation. Mol. Cell Biol., 19:1751-58, 1999; Blattner et al., DNA damage induced p53 stabilization: no indication for an involvement of p53 phosphorylation. Oncogene, 18:1723-32, 1999; Dumaz and Meek, Serine15 phosphorylation stimulates p53 transactivation but does not directly influence interaction with HDM2. EMBO J., 18:7002-10, 1999; Ashcroft et al., Stress signals utilize multiple pathways to stabilize p53. Mol. Cell Biol., 20:3224-33, 2000). However, the precise mechanism by which p53 is activated by cellular stress is not completely understood; it is generally thought to involve mainly post-translational modifications of p53, including phosphorylation, acetylation, and ubiquitination (Appella and Anderson, Signaling to p53: breaking the posttranslational modification code. Pathol. Biol. (Paris), 48:227-45, 2000; Giaccia and Kastan, The complexity of p53 modulation: emerging patterns from divergent signals. Genes Dev., 12:2973-83, 1998). For example, in response to DNA damage, p53 is phosphorylated at multiple sites; these phosphorylation events promote p53 stabilization by preventing binding with Mdm2, thereby rendering p53 more resistant to Mdm2-mediated degradation (Shieh et al., supra; Appella and Anderson, supra).

By serving as a signal for specific cellular-protein degradation, ubiquitination plays a critical role in physiological regulation of many cellular processes (Hershko et al., The ubiquitin system. *Nat. Med.*, 6:1073-81, 2000; Laney and Hochstrasser, Substrate targeting in the ubiquitin system. *Cell*, 97:427-30, 1999; Kornitzer and Ciechanover, Modes of regulation of ubiquitin-mediated protein degradation. *J. Cell. Phys.*, 182:1-11, 2000). The ubiquitination of p53 was first discovered in papilloma-virus-infected cells, through the functions mediated by the viral E6 protein (Scheffner et al., The HPV-16 E6 and E6-AP complex functions as an ubiquitin-protein ligase in the ubiquitination of p53. *Cell*, 75:495-505, 1993). However, in normal cells, Mdm2 functions as a ubiquitin ligase (E3) that directly mediates p53 ubiquitination and subsequent degradation (Haupt et al., Mdm2 promotes the rapid degradation of p53. *Nature*, 387:296-99, 1997; Kubbutat et al., Regulation of p53 stability by Mdm2. *Nature*, 387:299-303, 1997; Honda et al., Oncoprotein MDM2 is a ubiquitin ligase E3 for tumor suppressor p53. *FEBS Lett.*, 420:25-27, 1997). Furthermore, by inhibiting Mdm2-mediated ubiquitin ligase activity, the p14ARF tumor suppressor can stabilize p53 in vivo in response to oncogene activation (Sherr and Webber, The ARF/p53 pathway. *Curr. Opin. Genet. Dev.*, 10:94-99, 2000).

As indicated above, evidence suggests that, in cells that retain wild-type p53, other defects in the p53 pathway may play an important role in tumorigenesis. To date, at least one method of treating cancer has been developed that targets the p53 pathway. This treatment involves the stabilization of p53 by inhibiting Mdm2-mediated deubiquitination. It is estimated that 15-30% of all tumor cases exhibit overexpression of Mdm2. However, this enzyme is notoriously difficult to inhibit. Moreover, recent studies imply the existence of an alternative mechanism for p53 stabilization that may function even when the Mdm2-mediated ubiquitination pathway is intact (Ashcroft et al., 1999, supra; Blattner et al., supra; Dumaz and Meek, supra; Ashcroft et al., 2000, supra). Accordingly, while regulation of the p53 pathway is of intense interest, and presents a potential means of diagnosing and treating cancers, a greater understanding of this pathway and the regulation of p53 ubiquitination would provide a valuable basis upon which new diagnostic and therapeutic methods may be developed.

SUMMARY OF THE INVENTION

The present invention is based upon the discovery that HAUSP deubiquitinates p53, thereby stabilizing p53 and rendering it available for tumor-suppressor activity. This discovery has broad implications in the diagnosis, monitoring, and treatment of neoplasias, particularly cancers associated with p53.

Accordingly, the present invention provides a method for determining whether a subject has neoplasia, by assaying a diagnostic sample of the subject for HAUSP expression, wherein detection of HAUSP expression is diagnostic of neoplasia in the subject.

The present invention also provides a method for assessing the efficacy of therapy to treat neoplasia in a subject who has undergone or is undergoing treatment for neoplasia, by assaying a diagnostic sample of the subject for HAUSP expression, wherein normal HAUSP expression in the diagnostic sample is indicative of successful therapy, and HAUSP expression elevated above normal in the diagnostic sample is indicative of a need to continue therapy to treat neoplasia.

The present invention further provides a method for assessing the prognosis of a subject who has neoplasia, by assaying a diagnostic sample of the subject for HAUSP expression, wherein the subject's prognosis improves with a decrease in HAUSP expression in the diagnostic sample, the subject's prognosis worsens with an increase in HAUSP expression in the diagnostic sample.

The present invention also provides a kit for use in detecting neoplasia, comprising: (a) an agent reactive with HAUSP; and (b) reagents suitable for detecting expression of HAUSP.

Additionally, the present invention provides a method for treating neoplasia in a subject in need of treatment, by increasing activity of HAUSP in the subject. Also provided is a pharmaceutical composition, comprising a modulator of HAUSP expression or a HAUSP protein, in an amount effective to treat neoplasia in a subject to whom the composition is administered, and a pharmaceutically-acceptable carrier.

The present invention further provides a method for deubiquitinating p53 in a cell, by contacting the cell with HAUSP, in an amount effective to deubiquitinate p53. Also provided is a method for treating neoplasia in a subject in need of treatment, by deubiquitinating p53 in a cell of the subject.

Additionally, the present invention is directed to a method for identifying an agent that is reactive with p53, by: (a) contacting a candidate agent with p53, in the presence of HAUSP; and (b) assessing the ability of the candidate agent to inhibit HAUSP-p53 interaction. Optionally, this method of the present invention may further comprise the steps of: (c) contacting the candidate agent with one or more cells containing p53; and (d) determining if the agent has an effect on a p53-associated biological event in the one or more cells. Also provided is an agent identified by this method of the present invention.

The present invention further provides a method for treating a p53-associated condition in a subject in need of treatment, by administering to the subject an amount of the agent of claim 43 effective to treat the p53-associated condition in the subject.

The present invention also provides a complex comprising p53 and HAUSP, and a mutant HAUSP comprising the HAUSP amino acid sequence, in which Ser is substituted for Cys at amino acid residue 223.

Finally, the present invention is directed to a transgenic non-human animal whose genome comprises a disruption in its endogenous HAUSP gene, wherein the transgenic animal exhibits decreased expression of functional HAUSP protein relative to wild-type.

Additional aspects of the present invention will be apparent in view of the description which follows.

Figure 1:
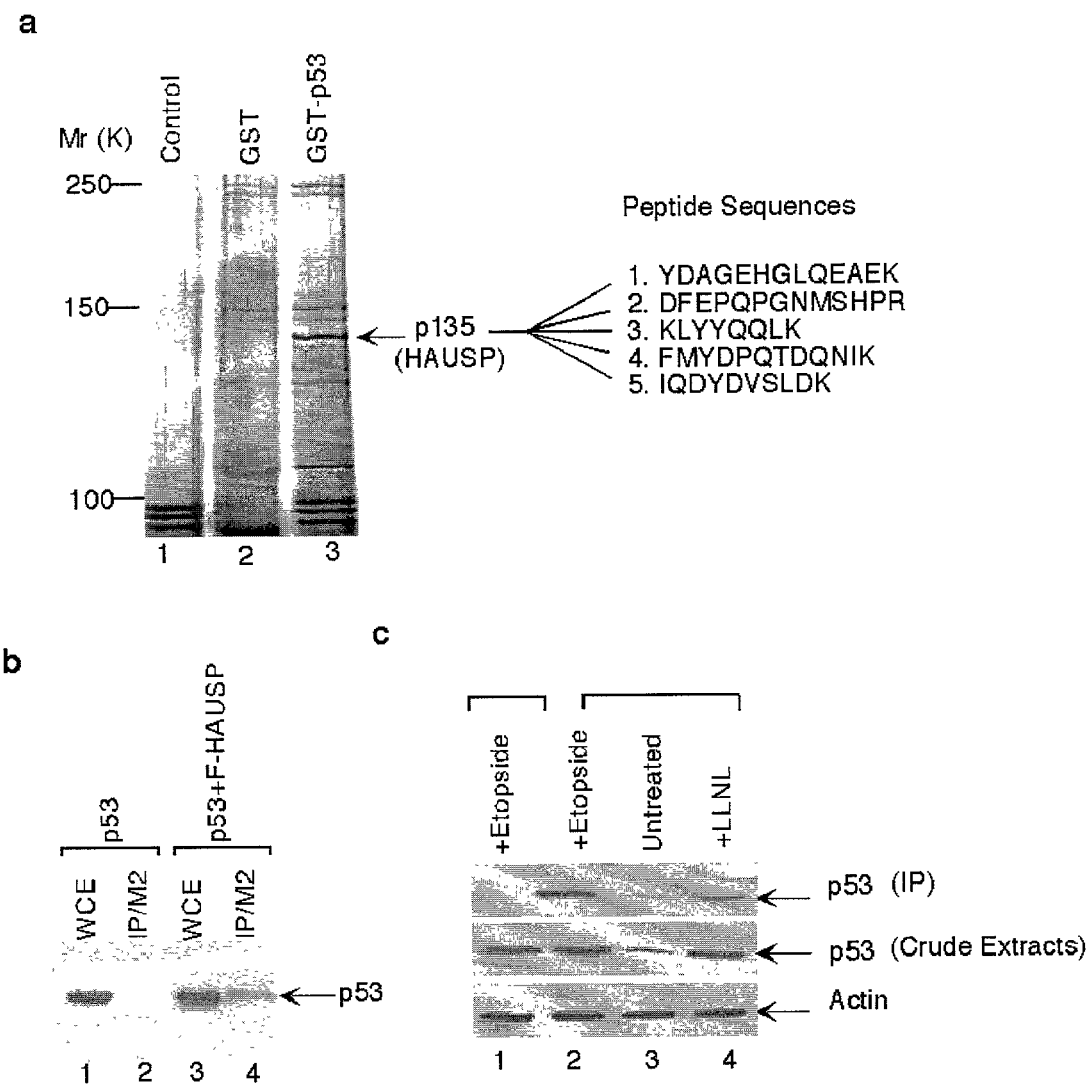
FIGS. 1A-1C illustrate purification of HAUSP, and interactions between p53 and HAUSP. (A) HAUSP was identified as a p53-binding protein, using silver-staining analysis of a SDS-PAGE gel containing the eluates from the indicated columns. Peptide sequences (SEQ ID NOs: 1-5) derived from the p135 protein band were obtained from mass spectrometry. The peptide sequences are as follows: YDAGEHGLQEAEK (SEQ ID NO:1); DFEPQPGNMSHIPR (SEQ ID NO:2); KLYYQQLK (SEQ ID NO:3); FMYDPQTDQNIK (SEQ ID NO:4); and IQDYDVSLDK (SEQ ID NO:5). (B) It was determined that p53 interacts with HAUSP in cells, using Western blot analysis of the whole cell extract (WCE) or immunoprecipitates (IP/M2) from the transfected cells by anti-p53 monoclonal antibody (DO-1). (C) The interaction between the endogenous p53 and HAUSP proteins was elucidated using Western blot analyses of control immunoprecipitates with the pre-immunoserum (lane 1, upper), or Western blot analyses of immunoprecipitates with the anti-HAUSP antibody (IP/α-HAUSP) from untreated cells (lane 3, upper) or cells treated with a DNA-damage reagent (Etoposide) (lane 2, upper) or H460 cells treated with a proteasome inhibitor (LLNL) (lane 4, upper), or Western blot analyses of these different nuclear extracts (NE) immunoprecipitated by the anti-p53 (middle panels) or anti-actin monoclonal antibody (lower panels).

FIGS. 2A-2F demonstrate that HAUSP interacts with, and stabilizes, p53 in vivo. HAUSP enhanced the steady-state levels of p53 (A), but not p27 (B), according to Western blot analyses of cell extracts from the H1299 cells transfected with p53 alone (lanes 1, 3), or cotransfected with p53 and HAUSP (lanes 2, 4), with the anti-p53 monoclonal antibody (DO-1). (A) Western blot analysis of cell extracts from the H1299 cells transfected with p27 alone (lanes 1, 3), or cotransfected with p27 and HAUSP (lanes 2, 4), with the anti-p27 monoclonal antibody (B). (C) Protection of p53 from Mdm2-mediated degradation by HAUSP was illustrated using Western blot analysis of extracts from the cells transfected with p53 (lane 1), or cotransfected with p53 and HAUSP (lane 2), or cotransfected with p53 and Mdm2 (lane 3), or in combination with different amounts of HAUSP (lanes 4-6), by the anti-p53 monoclonal antibody (DO-1). (D) HAUSP regulates the expression levels of endogenous proteins, as shown in cell extracts from both mock-infected and pBabe-HAUSP-infected IMR-90 cells, which were analyzed for expression levels of each protein by Western blot analysis. (E) Regulation of the half-life of endogenous p53 by HAUSP. Cell extracts from both mock-infected and pBabe-HAUSP-infected IMR-90 cells, harvested at different time points as indicated after pre-treatment with cyclohexamide (CHX), were analyzed for p53 protein levels by Western blot with anti-p53 (DO-1). (F) Regulation of the ubiquitination levels of endogenous p53 by HAUSP. Cell extracts from mock-infected cells, and from pBabe-HAUSP-infected IMR-90 cells pre-treated with LLNL for 4 h, were first immunoprecipitated with anti-p53 polyclonal antibody, and then analyzed for ubiquitination levels by Western blot with anti-p53 (DO-1).

FIGS. 3A-3B depicts the effects of HAUSP on p53-mediated cell-growth repression (A) and apoptosis (B). (A) A pair of human lung carcinoma cells (H1299 and H460) and a pair of mouse embryo fibroblasts (MEF p53(+/+) and MEF p53(−/−)) were either infected with pBabe-vector, or with pBabe-HAUSP. At 24 h post-infection, cells were split and kept in the medium with puromycin, and surviving colonies were counted after 2 weeks. (B) H1299 cells were transfected with p53 alone or HAUSP alone, or cotransfected with p53 and Mdm2, or cotransfected with p53, Mdm2, and HAUSP, as indicated. After transfection, the cells were fixed, stained for p53 by FITC-conjugated α-p53 antibody, and analyzed for apoptotic cells (subG1) according to DNA content (PI staining).

Figure 4:
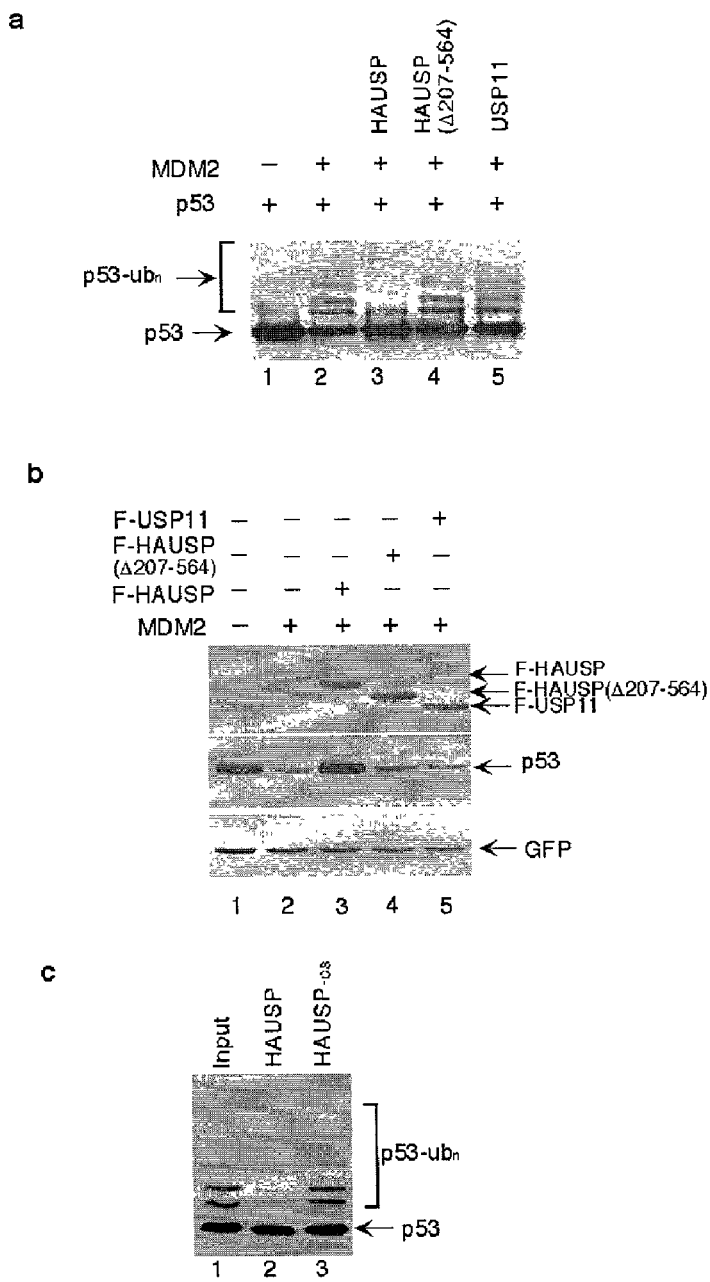

FIGS. 4A-4C illustrate deubiquitination of p53 by HAUSP, both in vivo and in vitro. (A) Regulation of p53 ubiquitination levels in vivo. Western blot analysis of immunoprecipitates with the M2/Flag antibody from the cells transfected with Flag-p53 (lane 1), or cotransfected with Flag-p53 and Mdm2 (lane 2), or in combination with different expression vectors as indicated (lanes 3-5), by the anti-p53 monoclonal antibody (DO-1). (B) Regulation of p53 stability by the HAUSP mutant. Western blot analysis of H1299 cell extracts from the cells transfected with p53 (lane 1), or cotransfected with p53 and Mdm2 (lane 2), or in combination with different expression vectors as indicated (lanes 3-5), by the anti-p53 monoclonal antibody (DO-1). The CMV-GFP expression vector was included in each transfection for a transfection-efficiency control, and the levels of GFP were detected with the anti-GFP monoclonal antibody (JL-8, Clontech). (C) In vitro deubiquitination of p53 by HAUSP. The purified ubiquitinated p53 protein was incubated with the purified recombinant proteins of either HAUSP (lane 2) or HAUSP-cs (lane 3).

FIGS. 5A-5D demonstrate the dominant negative effects of HAUSP-cs in human cells. (A) Western blot analysis of immunoprecipitates with the M2/Flag antibody from the cells transfected with Flag-p53 (lane 1), or cotransfected with Flag-p53 and Mdm2 (lane 2), or in combination with HAUSP and HAUSP-cs as indicated (lanes 3, 4), by the anti-p53 monoclonal antibody (DO-1). All cells were treated with LLNL (50 mM) for 4 h before harvest. (B) Western blot analysis of immunoprecipitates with M2/Flag antibody from human SJSA cells either transfected with expression vectors of Flag-p53 (lanes 2, 4) or cotransfected with expression vectors of Flag-p53 with HAUSP-cs (lanes 1, 3), by the anti-p53 monoclonal antibody (DO-1). The CMV-GFP expression vector was included in each transfection, for a transfection-efficiency control, and the levels of GFP were detected with the anti-GFP monoclonal antibody (JL-8, Clontech). (C) Western blot analysis of the cell extracts from both mock-infected and pBabe-HAUSP-cs-infected IMR-90 cells by anti-p53 monoclonal antibody (DO-1). Cells were either not treated (lanes 1,2) or treated with 20 mM of Etoposide (lanes 3-6), for either 1 h or 2 h as indicated. (D) A model for regulation of p53 stability by Mdm2, HAUSP, and ARF. p53 is ubiquitinated by Mdm2, and subsequently degraded by the 26S proteasome, while the ARF tumor suppressor induces p53 stabilization through inhibition of Mdm2-mediated ubiquitin ligase activity. HAUSP can directly deubiquitinate p53, and rescue the ubiquitinated p53 from degradation.

FIG. 6 sets forth the amino acid sequence of human HAUSP (SEQ ID NO:6).

FIG. 7 sets forth the cDNA sequence of human HAUSP (SEQ ID NO:7).

Figure 8:
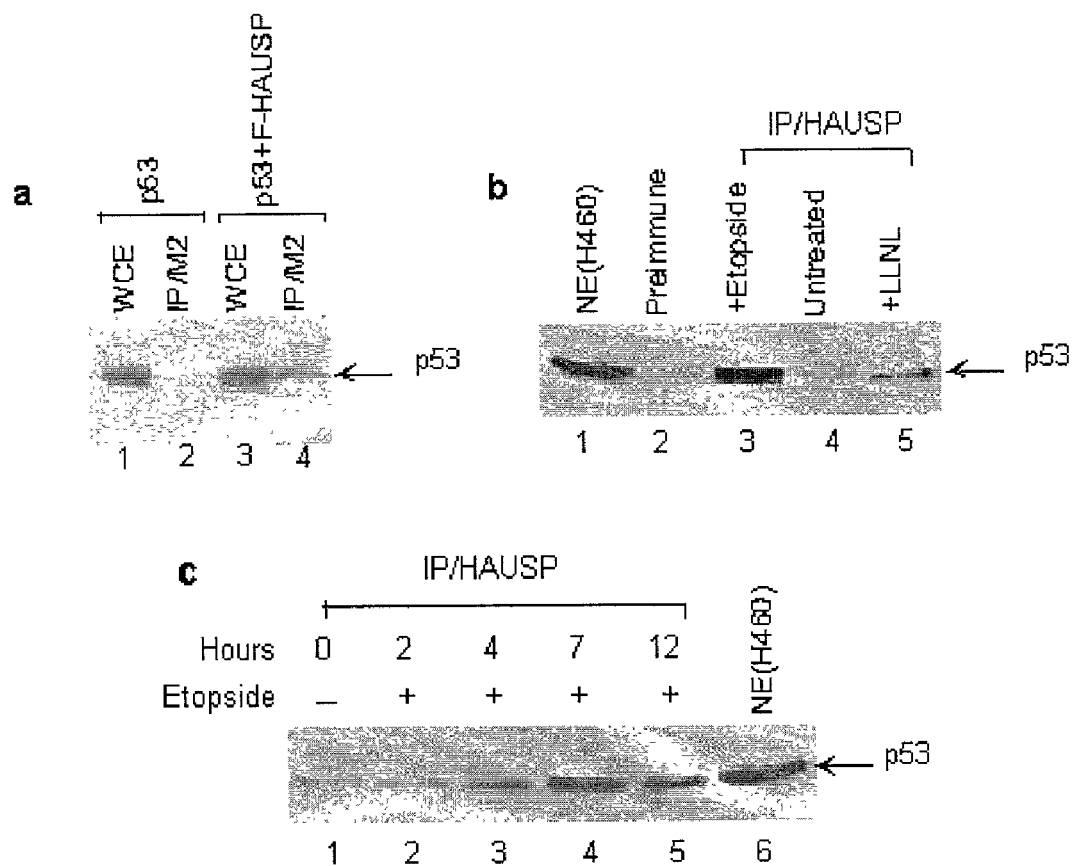

FIGS. 8A-8C illustrate p53 interaction with HAUSP in vivo. (A) p53 interacts with HAUSP in cells. Western blot analyses of the indicated whole cell extract (WCE) (lanes 1, 3) or the immunoprecipitates with M2 antibody (IP/M2) (lanes 2, 4) prepared from either F-HAUSP and p53 cotransfected H1299 cells (lanes 3, 4) or the p53-alone transfected cells (lanes 1, 2) with anti-p53 monoclonal antibody (DO-1). (B) The interaction between the endogenous p53 and HAUSP proteins. Western blot analyses of the indicated nuclear extract (NE) (lanes 1), or control immunoprecipitates with pre-immunoserum (lane 2), or immunoprecipitates with anti-HAUSP antibody (IP/HAUSP) from cell extracts of either untreated (lane 4), DNA-damage-treated, or LLNL-treated H460 cells with the anti-p53 monoclonal antibody. (c) The interaction between p53 and HAUSP during the DNA damage response. Western blot analyses of the H460 nuclear extract (NE) (lanes 6), or immunoprecipitates with anti-HAUSP antibody (IP/α-HAUSP) (lanes 1-5) derived from 460 cells harvested at the indicated time points after the DNA-damage treatment with the anti-p53 monoclonal antibody.

FIGS. 9A-9B depict in vitro interaction of p53 with HAUSP. (A) GST and GST-p53 fusion proteins were used in a GST pull-down assay with in vitro translated $^{35}$S-labeled full length HAUSP(FL) (lanes 1-3), or the N-terminal extension of HAUSP (1-248) (lanes 4-6), or the core domain (245-

644) of HAUSP (M) (lanes 7-9), or the C-terminal extension of HAUSP (637-1102). (B) The in vitro interaction of p53 with HAUSP-cs, HAUSP(Δ207-564), and USP11. The GST and GST-p53 fusion proteins were used in a GST pull-down assay within vitro translated $^{35}$S-labeled HAUSP-cs (lanes 1-3), HAUSP(Δ207-564) (lanes 4-6), or USP11 (lanes 7-9).

DETAILED DESCRIPTION OF THE INVENTION

The present invention provides a method for determining whether a subject has neoplasia. As used herein, the "subject" is a mammal, including, without limitation, a cow, dog, human, monkey, mouse, pig, or rat. Preferably, the subject is a human. The inventors have demonstrated herein (see, e.g., FIGS. 8A-8C) significant enhancement of HAUSP-p53 interaction, and enhanced HAUSP expression, in cells subjected to DNA damage, as compared with normal (undamaged) cells. Accordingly, the method of the present invention comprises assaying a diagnostic sample of the subject for expression of HAUSP, wherein detection of HAUSP expression elevated above normal is diagnostic of neoplasia in the subject.

As used herein, "HAUSP" includes both a HAUSP (herpesvirus-associated ubiquitin-specific protease) protein and a HAUSP analogue. Unless otherwise indicated, "protein" shall include a protein, protein domain, polypeptide, or peptide. As further used herein, the HAUSP protein (also known as USP7) has the amino acid sequence set forth in FIG. 6 (SEQ ID NO:6; see, also, Everett et al., supra and GenBank Accession No. CAA96580), including conservative substitutions thereof). A "HAUSP analogue", as used herein, is a functional variant of the HAUSP protein, having HAUSP biological activity, that has 60% or greater (preferably, 70% or greater) amino-acid-sequence homology with the HAUSP protein. A HAUSP "analogue" includes a variant of the HAUSP protein that has a homologous three-dimensional conformation. As further used herein, the term "HAUSP biological activity" refers to the activity of a protein or peptide that demonstrates an ability to associate physically with p53 tumor-suppressor protein (i.e., binding of approximately two fold, or, more preferably, approximately five fold, above the background binding of a negative control), as described herein. HAUSP and HAUSP analogues may be produced synthetically or recombinantly, or may be isolated from native cells. HAUSP is preferably produced recombinantly, using conventional techniques and cDNA encoding HAUSP—which may be produced from HAUSP cDNA (SEQ ID NO:7; see, also, Everett et al., supra and GenBank Accession No. Z72499).

As used herein, "conservative substitutions" are those amino acid substitutions which are functionally equivalent to the substituted amino acid residue, either because they have similar polarity or steric arrangement, or because they belong to the same class as the substituted residue (e.g., hydrophobic, acidic, or basic). The term "conservative substitutions", as defined herein, includes substitutions having an inconsequential effect on the ability of HAUSP to interact with p53, particularly in respect of the use of said interaction for the identification and design of p53 inhibitors, for molecular replacement analyses, and/or for homology modeling.

The method of the present invention may be used to determine whether a subject has neoplasia, thereby permitting the diagnosis of such neoplasia in the subject. As used herein, "neoplasia" refers to the uncontrolled and progressive multiplication of tumor cells, under conditions that would not elicit, or would cause cessation of, multiplication of normal cells. Neoplasia results in a "neoplasm", which is defined herein to mean any new and abnormal growth, particularly a new growth of tissue, in which the growth of cells is uncontrolled and progressive. Thus, neoplasia includes "cancer", which herein refers to a proliferation of tumor cells having the unique trait of loss of normal controls, resulting in unregulated growth, lack of differentiation, local tissue invasion, and/or metastasis.

As used herein, neoplasms include, without limitation, morphological irregularities in cells in tissue of a subject, as well as pathologic proliferation of cells in tissue of a subject, as compared with normal proliferation in the same type of tissue. Additionally, neoplasms include benign tumors and malignant tumors (e.g., breast tumors) that are either invasive or noninvasive. Malignant neoplasms are distinguished from benign in that the former show a greater degree of anaplasia, or loss of differentiation and orientation of cells, and have the properties of invasion and metastasis. Examples of neoplasms or neoplasias which may be assessed, detected, diagnosed, monitored, or treated in accordance with inventions described herein include, without limitation, carcinomas, particularly those of the bladder, breast, cervix, colon, head, kidney, lung, neck, ovary, prostate, and stomach; lymphocytic leukemias, particularly acute lymphoblastic leukemia and chronic lymphocytic leukemia; myeloid leukemias, particularly acute monocytic leukemia, acute promyelocytic leukemia, and chronic myelocytic leukemia; malignant lymphomas, particularly Burkitt's lymphoma and Non-Hodgkin's lymphoma; malignant melanomas; myeloproliferative diseases; sarcomas, particularly Ewing's sarcoma, hemangiosarcoma, Kaposi's sarcoma, liposarcoma, peripheral neuroepithelioma, and synovial sarcoma; and mixed types of neoplasias, particularly carcinosarcoma and Hodgkin's disease (Beers and Berkow (eds.), *The Merck Manual of Diagnosis and Therapy*, 17$^{th}$ ed. (Whitehouse Station, N.J.: Merck Research Laboratories, 1999) 973-74, 976, 986, 988, 991).

As indicated above, over 60% of all cancer cases are associated with p53 mutations. Accordingly, in one embodiment of the present invention, the methods and compositions of the present invention are directed to the assessment, detection, diagnosis, monitoring, and treatment of p53-associated neoplasias, including neoplasias associated with a defect in the p53 pathway. In another embodiment of the present invention, the methods and compositions of the present invention are directed to the assessment, detection, diagnosis, monitoring, and treatment of breast cancer, colon cancer, leukemia, lung cancer, malignant melanoma, ovarian cancer, or prostate cancer.

According to the method of the present invention, the diagnostic sample of a subject may be assayed in vitro or in vivo. Where the assay is performed in vitro, a diagnostic sample from the subject may be removed using standard procedures. The diagnostic sample may be tissue, including any bone, brain tissue, breast tissue, colon tissue, muscle tissue, nervous tissue, ovarian tissue, prostate tissue, retinal tissue, skin tissue, or soft tissue, which may be removed by standard biopsy. In addition, the diagnostic sample may be a bodily fluid, including cerebrospinal fluid, pericardial fluid, peritoneal fluid, saliva, serum, and urine. Furthermore, the diagnostic sample taken from the subject or patient may be, for example, any tissue known to have a neoplasm, any tissue suspected of having a neoplasm, or any tissue believed not to have a neoplasm.

Protein may be isolated and purified from the diagnostic sample of the present invention using standard methods known in the art, including, without limitation, extraction from a tissue (e.g., with a detergent that solubilizes the protein) where necessary, followed by affinity purification on a column, chromatography (e.g., FTLC and HPLC), immunoprecipitation (with an antibody to HAUSP), and precipitation (e.g., with isopropanol and a reagent such as Trizol). Isolation and purification of the protein may be followed by electrophoresis (e.g., on an SDS-polyacrylamide gel). Nucleic acid may be isolated from a diagnostic sample using standard techniques known to one of skill in the art.

In accordance with the method of the present invention, neoplasia in a subject may be diagnosed by assaying a diagnostic sample of the subject for expression of HAUSP, wherein expression of HAUSP elevated above normal is diagnostic of neoplasia. As used herein, "expression" means the transcription of the HAUSP gene into at least one mRNA transcript, or the translation of at least one mRNA into a HAUSP protein, as defined above. Accordingly, a diagnostic sample may be assayed for HAUSP expression by assaying for HAUSP protein, HAUSP cDNA, or HAUSP mRNA. The appropriate form of HAUSP will be apparent based on the particular techniques discussed herein.

Furthermore, it is contemplated that the diagnostic sample may be assayed for expression of any or all forms of HAUSP protein (including precursor, endoproteolytically-processed forms, and other forms resulting from post-translational modification) in order to determine whether a subject or patient has neoplasia. It is also contemplated that the diagnostic sample may be assayed for expression of HAUSP elevated above normal by detecting an increase in p53-HAUSP interaction, as disclosed herein. Accordingly, in one embodiment of the present invention, HAUSP expression elevated above normal is detected by detecting p53-HAUSP interaction elevated above normal.

As used herein, the term "elevated above normal" means expression of HAUSP (or p53-HAUSP interaction) is detected at a level that is significantly greater than the level expected for the same type of diagnostic sample taken from a nondiseased subject or patient (i.e., one who does not have neoplasia) of the same gender and of similar age. As further used herein, "significantly greater" means that the difference between the level of HAUSP expression (or p53-HAUSP interaction) that is elevated above normal, and the expected (normal) level of HAUSP (or p53-HAUSP interaction), is of statistical significance. Preferably, HAUSP expression (or p53-HAUSP interaction) elevated above normal is expression of HAUSP (or p53-HAUSP interaction) at a level that is at least 10% greater than the level of HAUSP expression (or p53-HAUSP interaction) otherwise expected. Where HAUSP expression (or p53-HAUSP interaction) is expected to be absent from a particular diagnostic sample taken from a particular subject or patient, the normal level of HAUSP expression (or p53-HAUSP interaction) for that subject or patient is nil. Where a particular diagnostic sample taken from a particular subject or patient is expected to have a low level of constitutive HAUSP expression (or p53-HAUSP interaction), that low level is the normal level of HAUSP expression (or p53-HAUSP interaction) for that subject or patient. As disclosed herein, HAUSP-p53 interactions, and HAUSP expression, are generally present at low levels in cells that do not contain DNA damage.

Expected or normal levels of HAUSP expression for a particular diagnostic sample taken from a subject or patient may be easily determined by assaying nondiseased subjects of a similar age and of the same gender. For example, diagnostic samples may be obtained from at least 30 normal, healthy men between the ages of 25 and 80, to determine the normal quantity of HAUSP expression in males. A similar procedure may be followed to determine the normal quantity of HAUSP expression in females. Once the necessary or desired samples have been obtained, the normal quantities of HAUSP expression in men and women may be determined using a standard assay for quantification, such as flow cytometry, Western blot analysis, or an ELISA for measuring protein quantities, as described below. For example, an ELISA may be run on each sample in duplicate, and the means and standard deviations of the quantity of the HAUSP protein may be determined. If necessary, additional subjects may be recruited before the normal quantities of HAUSP expression are quantified. A similar type of procedure may be used to determine expected or normal levels of p53-HAUSP interaction for a particular diagnostic sample taken from a subject or patient.

In accordance with the method of the present invention, a diagnostic sample of a subject may be assayed for HAUSP expression (or p53-HAUSP interaction), and HAUSP expression (or p53-HAUSP interaction) may be detected in a diagnostic sample, using assays and detection methods readily determined from the known art (e.g., immunological techniques, hybridization analysis, fluorescence imaging techniques, and/or radiation detection, etc.), as well as any assays and detection methods disclosed herein (e.g., immunoprecipitation, Western blot analysis, etc.). For example, a diagnostic sample of a subject may be assayed for HAUSP expression using an agent reactive with HAUSP. As used herein, "reactive" means the agent has affinity for, binds to, or is directed against HAUSP. As further used herein, an "agent" shall include a protein, polypeptide, peptide, nucleic acid (including DNA or RNA), antibody, Fab fragment, $F(ab')_2$ fragment, molecule, compound, antibiotic, drug, and any combinations thereof. A Fab fragment is a univalent antigen-binding fragment of an antibody, which is produced by papain digestion. A $F(ab')_2$ fragment is a divalent antigen-binding fragment of an antibody, which is produced by pepsin digestion. Preferably, the agent of the present invention is labeled with a detectable marker or label.

In one embodiment of the present invention, the agent reactive with HAUSP is an antibody. As used herein, the antibody of the present invention may be polyclonal or monoclonal. In addition, the antibody of the present invention may be produced by techniques well known to those skilled in the art. Polyclonal antibody, for example, may be produced by immunizing a mouse, rabbit, or rat with purified HAUSP. Monoclonal antibody then may be produced by removing the spleen from the immunized mouse, and fusing the spleen cells with myeloma cells to form a hybridoma which, when grown in culture, will produce a monoclonal antibody.

The antibodies used herein may be labeled with a detectable marker or label. Labeling of an antibody may be accomplished using one of a variety of labeling techniques, including peroxidase, chemiluminescent labels known in the art, and radioactive labels known in the art. The detectable marker or label of the present invention may be, for example, a nonradioactive or fluorescent marker, such as biotin, fluorescein (FITC), acridine, cholesterol, or carboxy-X-rhodamine, which can be detected using fluorescence and other imaging techniques readily known in the art. Alternatively, the detectable marker or label may be a radioactive marker, including, for example, a radioisotope. The radioisotope may be any isotope that emits detectable radiation, such as $^{35}S$, $^{32}P$, $^{125}I$, $^{3}H$, or $^{14}C$. Radioactivity emitted by the radioisotope can be detected by techniques well known in the art. For example, gamma emission from the radioisotope may be detected using gamma imaging techniques, particularly scintigraphic imaging. Preferably, the agent of the present invention is a high-affinity antibody (e.g., α-HAUSP) labeled with a detectable marker or label.

Where the agent of the present invention is an antibody reactive with HAUSP, a diagnostic sample taken from the subject may be purified by passage through an affinity column which contains HAUSP antibody (e.g., α-HAUSP) as a ligand attached to a solid support, such as an insoluble organic polymer in the form of a bead, gel, or plate. The antibody attached to the solid support may be used in the form of a column. Examples of suitable solid supports include, without limitation, agarose, cellulose, dextran, polyacrylamide, polystyrene, sepharose, or other insoluble organic polymers. The HAUSP antibody (e.g., α-HAUSP) may be further attached to the solid support through a spacer molecule, if desired. Appropriate binding conditions (e.g., temperature, pH, and salt concentration) for ensuring binding of the agent and the antibody may be readily determined by the skilled artisan. In a preferred embodiment, the HAUSP antibody (e.g., α-HAUSP) is attached to a sepharose column, such as Sepharose 4B.

Where the agent is an antibody, a diagnostic sample of the subject may be assayed for HAUSP expression using binding studies that utilize one or more antibodies immunoreactive with HAUSP, along with standard immunological detection techniques. For example, the HAUSP protein eluted from the affinity column may be subjected to an ELISA assay, Western blot analysis, flow cytometry, or any other immunostaining method employing an antigen-antibody interaction. Preferably, the diagnostic sample is assayed for HAUSP expression using Western blotting.

Alternatively, a diagnostic sample of a subject may be assayed for HAUSP expression using hybridization analysis of nucleic acid extracted from the diagnostic sample taken from the subject. According to this method of the present invention, the hybridization analysis may be conducted using Northern blot analysis of mRNA. This method also may be conducted by performing a Southern blot analysis of DNA using one or more nucleic acid probes, which hybridize to nucleic acid encoding HAUSP. The nucleic acid probes may be prepared by a variety of techniques known to those skilled in the art, including, without limitation, the following: restriction enzyme digestion of HAUSP nucleic acid; and automated synthesis of oligonucleotides having sequences which correspond to selected portions of the nucleotide sequence of the HAUSP nucleic acid, using commercially-available oligonucleotide synthesizers, such as the Applied Biosystems Model 392 DNA/RNA synthesizer.

The nucleic acid probes used in the present invention may be DNA or RNA, and may vary in length from about 8 nucleotides to the entire length of the HAUSP nucleic acid. The HAUSP nucleic acid used in the probes may be derived from mammalian HAUSP. The nucleotide sequence for human HAUSP is known (see, e.g., Everett et al., supra). Using this sequence as a probe, the skilled artisan could readily clone corresponding HAUSP cDNA from other species. In addition, the nucleic acid probes of the present invention may be labeled with one or more detectable markers or labels. Labeling of the nucleic acid probes may be accomplished using one of a number of methods known in the art—e.g., nick translation, end labeling, fill-in end labeling, polynucleotide kinase exchange reaction, random priming, or SP6 polymerase (for riboprobe preparation)—along with one of a variety of labels—e.g., radioactive labels, such as $^{35}S$, $^{32}P$, or $^{3}H$, or nonradioactive labels, such as biotin, fluorescein (FITC), acridine, cholesterol, or carboxy-X-rhodamine (ROX). Combinations of two or more nucleic acid probes (or primers), corresponding to different or overlapping regions of the HAUSP nucleic acid, also may be used to assay a diagnostic sample for HAUSP expression, using, for example, PCR or RT-PCR.

The detection of HAUSP expression (or p53-HAUSP interaction) in the method of the present invention may be followed by an assay to measure or quantify the extent of HAUSP expression in a diagnostic sample of a subject. Such assays are well known to one of skill in the art, and may include immunohistochemistry/immunocytochemistry, flow cytometry, mass spectroscopy, Western blot analysis, or an ELISA for measuring amounts of HAUSP protein. For example, to use an immunohistochemistry assay, histological (paraffin-embedded) sections of tissue may be placed on slides, and then incubated with an antibody against HAUSP. The slides then may be incubated with a second antibody (against the primary antibody), which is tagged to a dye or other calorimetric system (e.g. a fluorochrome, a radioactive agent, or an agent having high electron-scanning capacity), to permit visualization of HAUSP present in the sections.

It is contemplated that the diagnostic sample in the present invention frequently will be assayed for HAUSP expression (or p53-HAUSP interaction) not by the subject or patient, nor by his/her consulting physician, but by a laboratory technician or other clinician. Accordingly, the method of the present invention further comprises providing to a subject's or patient's consulting physician a report of the results obtained upon assaying a diagnostic sample of the subject or patient for HAUSP expression.

The present invention further provides a method for assessing the efficacy of therapy to treat neoplasia in a subject or patient who has undergone or is undergoing treatment for neoplasia. The method of the present invention comprises assaying a diagnostic sample of the subject or patient for HAUSP expression, wherein detection of a normal level of HAUSP expression is indicative of successful therapy to treat neoplasia, and detection of HAUSP expression elevated above normal is indicative of a need to continue therapy to treat neoplasia. In one embodiment of the present invention, HAUSP expression elevated above normal is detected by detecting p53-HAUSP interaction elevated above normal. The neoplasia may be any of those described above, including p53-associated neoplasias. The diagnostic sample may be a tissue or a bodily fluid, as described above, and may be assayed for expression of HAUSP (or p53-HAUSP interaction) in vitro or in vivo. In addition, the diagnostic sample may be assayed for expression of HAUSP (or p53-HAUSP interaction) using all of the various assays and methods of detection and quantification described above. This method of the present invention provides a means for monitoring the effectiveness of therapy to treat neoplasia by permitting the periodic assessment of levels of HAUSP expression (or p53-HAUSP interaction) in a diagnostic sample taken from a subject or patient.

According to the method of the present invention, a diagnostic sample of a subject or patient may be assayed, and levels of HAUSP expression (or p53-HAUSP interaction) may be assessed, at any time following the initiation of therapy to treat neoplasia. For example, levels of HAUSP expression (or p53-HAUSP interaction) may be assessed while the subject or patient is still undergoing treatment for neoplasia. Where levels of HAUSP expression (or p53-HAUSP interaction) detected in an assayed diagnostic sample of the subject or patient continue to remain elevated above normal, a physician may choose to continue with the subject's or patient's treatment for the neoplasia. Where levels of HAUSP expression (or p53-HAUSP interaction) in an assayed diagnostic sample of the subject or patient decrease through successive assessments, it may be an indication that the treatment for neoplasia is working, and that treatment doses could be decreased or even ceased. Where levels of HAUSP expression (or p53-HAUSP interaction) in an assayed diagnostic sample of the subject or patient do not rapidly decrease through successive assessments, it may be an indication that the treatment for neoplasia is not working, and that treatment doses could be increased. Where HAUSP expression (or p53-HAUSP interaction) is no longer detected in an assayed diagnostic sample of a subject or patient at levels elevated above normal, a physician may conclude that the treatment for neoplasia has been successful, and that such treatment may cease.

It is within the confines of the present invention to assess levels of HAUSP expression following completion of a subject's or patient's treatment for neoplasia, in order to determine whether the neoplasia has recurred in the subject or patient. Accordingly, an assessment of levels of HAUSP expression (or p53-HAUSP interaction) in an assayed diagnostic sample may provide a convenient way to conduct follow-ups of patients who have been diagnosed with neoplasias. Furthermore, it is within the confines of the present invention to use assessed levels of HAUSP expression (or p53-HAUSP interaction) in an assayed diagnostic sample as a clinical or pathologic staging tool, as a means of determining the extent of neoplasia in the subject or patient, and as a means of ascertaining appropriate treatment options.

A correlation exists, in general, between tumor burden and the survival of a patient who has cancer. Therefore, it is also contemplated in the present invention that assaying a diagnostic sample of a subject for HAUSP expression may be a useful means of providing information concerning the prognosis of a subject or patient who has neoplasia. Accordingly, the present invention further provides a method for assessing the prognosis of a subject who has neoplasia, comprising assaying a diagnostic sample of the subject for HAUSP expression, wherein the subject's prognosis improves with a decrease in HAUSP expression in the diagnostic sample of the subject, and the subject's prognosis worsens with an increase in HAUSP expression in the diagnostic sample of the subject. In one embodiment of the present invention, HAUSP expression elevated above normal is detected by detecting p53-HAUSP interaction elevated above normal. Suitable diagnostic samples, assays, and detection and quantification methods for use in the method of the present invention have already been described. This method of the present invention provides a means for determining the prognosis of a subject or patient diagnosed with neoplasia based upon the level of HAUSP expression (or p53-HAUSP interaction) in an assayed diagnostic sample of the subject or patient.

According to the method of the present invention, a diagnostic sample of a subject or patient may be assayed, and levels of HAUSP expression (or p53-HAUSP interaction) may be assessed, at any time during or following the diagnosis of neoplasia in the subject or patient. For example, levels of HAUSP expression (or p53-HAUSP interaction) in an assayed diagnostic sample may be assessed before the subject or patient undergoes treatment for neoplasia, in order to determine the subject's or patient's initial prognosis. Additionally, levels of HAUSP expression (or p53-HAUSP interaction) in an assayed diagnostic sample may be assessed while the subject or patient is undergoing treatment for neoplasia, in order to determine whether the subject's or patient's prognosis has become more or less favorable through the course of treatment.

For example, where levels of HAUSP expression (or p53-HAUSP interaction) detected in an assayed diagnostic sample of the subject or patient are, or continue to remain, significantly high, a physician may conclude that the subject's or patient's prognosis is unfavorable. Where HAUSP expression (or p53-HAUSP interaction) in an assayed diagnostic sample of the subject or patient decreases through successive assessments, it may be an indication that the subject's or patient's prognosis is improving. Where levels of HAUSP expression (or p53-HAUSP interaction) in an assayed diagnostic sample of the subject or patient do not decrease significantly through successive assessments, it may be an indication that the subject's or patient's prognosis is not improving. Finally, where HAUSP expression (or p53-HAUSP interaction) is low, or is normal, in a diagnostic sample of the subject or patient, a physician may conclude that the subject's or patient's prognosis is favorable.

The discovery that HAUSP can be detected in cells displaying neoplasias provides a means of identifying patients with neoplasias, and presents the potential for commercial application in the form of a test for the diagnosis of neoplasias. The development of such a test could provide general screening procedures. Such procedures can assist in the early detection and diagnosis of cancers, and can provide a method for the follow-up of patients in whom HAUSP expression (including p53-HAUSP interaction) elevated above normal has been detected.

Accordingly, the present invention further provides a kit for use as an assay of neoplasia, comprising an agent reactive with HAUSP and reagents suitable for detecting expression of HAUSP (and p53-HAUSP interaction). The agent may be any of those described above, and may be used in any of the above-described assays or methods for detecting or quantifying HAUSP expression. Preferably, the agent of the present invention is labeled with a detectable marker or label.

As indicated above, over 60% of all cancer cases are associated with p53 mutations. Therefore, p53 is the key for treating many cancers, and the p53 pathway is a particular focus of interest. p53 is generally not a stable protein; it has a half-life of approximately 20 minutes, and is degraded very rapidly by proteosomes in the protein-degradation pathway following ubiquitination (the binding of ubiquitin). It is believed that the stabilization of p53 is important for the protein's efficiency as a tumor suppressor.

The inventors have determined that HAUSP (or USP7) is capable of stabilizing the p53 tumor suppressor by removing ubiquitin from p53, and thereby rescuing p53 from protein degradation. Thus, HAUSP is a deubiquitinase. HAUSP significantly enhances the half-life of p53, increasing it from 20 min to 90 min. Interestingly, as described below, it also appears that HAUSP behaves as a tumor suppressor when its gene is expressed. The tumor-suppressor function of HAUSP is believed to depend on p53. While deubiquitinases have been identified in yeast, and are known to exist in mammalian cells, the discovery herein represents the first time, to the inventors' knowledge, that it has been demonstrated that a particular deubiquitinase has substrate specificity.

It is expected that some cancers associated with defects in the p53 pathway result not from a defect in p53, but from either a mutated HAUSP (e.g., a mutation resulting from a genetic alteration at the coding region) and/or a defect in HAUSP regulation at the expression level (e.g., a defect resulting from a genetic alteration at the promoter region of the HAUSP gene). In view of the foregoing, it is clear that modulation of the levels of HAUSP in cells provides a means for enhancing p53's tumor-suppressor function, and for supplementing this function with HAUSP's own tumor-suppressor activity. Accordingly, the present invention further provides a method for treating neoplasia in a subject in need of treatment therefor, comprising increasing activity of HAUSP in the subject. The neoplasia may be any of those described above, but is preferably a p53-associated neoplasia.

In accordance with the method of the present invention, activity of HAUSP in a subject may be increased by targeting HAUSP directly. Additionally, activity of HAUSP in a subject may be increased indirectly, by targeting an enzyme or other endogenous molecule that regulates or modulates the functions or levels of HAUSP in the subject. Preferably, HAUSP activity in the subject is enhanced by at least 10% in the method of the present invention. More preferably, HAUSP activity is enhanced by at least 20%.

For example, activity of HAUSP in a subject may be increased by directly or indirectly activating, facilitating, or stimulating one or more functions of HAUSP in the subject (e.g., by the modulation or regulation of proteins that interact with HAUSP). The term "activating", as used herein, means stimulating or inducing the functions of HAUSP in the subject, particularly the deubiquitination, and resulting stabilization, of p53. In the method of the present invention, HAUSP in a subject may be activated, for example, by administering to the subject a small molecule or protein mimetic that stimulates HAUSP or that is reactive with HAUSP, as defined above.

Activity of HAUSP in a subject also may be increased by directly or indirectly causing, inducing, or stimulating the upregulation of HAUSP expression within a subject. Accordingly, in one embodiment of the present invention, activity of HAUSP is increased in a subject by administering to the subject a modulator of HAUSP expression in an amount effective to treat the neoplasia in the subject. The modulator may be a protein, polypeptide, peptide, nucleic acid (including DNA or RNA), antibody, Fab fragment, F(ab')$_2$ fragment, molecule, compound, antibiotic, drug, or an agent reactive with HAUSP, as defined herein, that induces or upregulates HAUSP expression.

Modulators of HAUSP may be identified using a simple screening assay. For example, to screen for candidate modulators of HAUSP, human lung carcinoma cells (H1299) may be plated onto microtiter plates, then contacted with a library of drugs. Any resulting increase in, or upregulation of, HAUSP expression then may be detected using nucleic acid hybridization and/or immunological techniques known in the art, including an ELISA. Additional modulators of HAUSP expression may be identified using screening procedures well known in the art or disclosed herein. Modulators of HAUSP will be those drugs which induce or upregulate expression of HAUSP. In this manner, candidate modulators also may be screened for their ability to inhibit proliferation of neoplasms using HAUSP expression as an indicator that cell division or growth of cells in a neoplasm is decreasing in rate, or has stopped.

It is within the confines of the present invention that the modulator of HAUSP expression may be linked to another agent, or administered in combination with another agent, such as an antineoplastic drug or a ribozyme, in order to increase the effectiveness of the treatment of neoplasia, increase the efficacy of targeting, and/or increase the efficacy of p53 deubiquitination. Examples of antineoplastic drugs to which the modulator of HAUSP expression may be linked include, without limitation, carboplatin, cyclophosphamide, doxorubicin, etoposide, and vincristine.

Activity of HAUSP in a subject also may be increased in a subject by directly or indirectly increasing levels of HAUSP in vivo within the subject. By way of example, the level of HAUSP in a subject may be increased by administering HAUSP protein to the subject, in an amount effective to treat neoplasia in the subject. Similarly, the level of HAUSP in a subject may be increased by administering to the subject a nucleic acid sequence encoding HAUSP, in a manner permitting expression of HAUSP in the subject, and in an amount effective to treat the neoplasia.

The present invention contemplates the use of proteins and protein analogues generated by synthesis of polypeptides in vitro, e.g., by chemical means or in vitro translation of mRNA. For example, HAUSP may be synthesized by methods commonly known to one skilled in the art (*Modern Techniques of Peptide and Amino Acid Analysis* (New York: John Wiley & Sons, 1981; Bodansky, M., *Principles of Peptide Synthesis* (New York: Springer-Verlag N.Y., Inc., 1984). Examples of methods that may be employed in the synthesis of the amino acid sequences, and analogues of these sequences, include, but are not limited to, solid-phase peptide synthesis, solution-method peptide synthesis, and synthesis using any of the commercially-available peptide synthesizers. The amino acid sequences of the present invention may contain coupling agents and protecting groups, which are used in the synthesis of protein sequences, and which are well known to one of skill in the art.

In accordance with the method of the present invention, HAUSP protein may be administered to a subject who has neoplasia, either alone or in combination with one or more antineoplastic drugs used to treat neoplasias. Examples of antineoplastic drugs with which the HAUSP protein may be combined include, without limitation, carboplatin, cyclophosphamide, doxorubicin, etoposide, and vincristine.

In the method of the present invention, a modulator of HAUSP expression, a HAUSP protein, or a nucleic acid sequence encoding HAUSP is administered to a subject who has neoplasia in an amount effective to treat the neoplasia in the subject. As used herein, the phrase "effective to treat the neoplasia" means effective to ameliorate or minimize the clinical impairment or symptoms resulting from the neoplasia. For example, the clinical impairment or symptoms of the neoplasia may be ameliorated or minimized by diminishing any pain or discomfort suffered by the subject; by extending the survival of the subject beyond that which would otherwise be expected in the absence of such treatment; by inhibiting or preventing the development or spread of the neoplasia; or by limiting, suspending, terminating, or otherwise controlling the maturation and proliferation of cells in the neoplasm. The amount of modulator of HAUSP expression, HAUSP protein, or nucleic acid encoding HAUSP that is effective to treat neoplasia in a subject will vary depending on the particular factors of each case, including the type of neoplasia, the stage of neoplasia, the subject's weight, the severity of the subject's condition, and the method of administration. These amounts can be readily determined by the skilled artisan.

In the method of the present invention, the modulator of HAUSP expression, the HAUSP protein, or the nucleic acid sequence encoding HAUSP may be administered to a human or animal subject by known procedures, including, without limitation, oral administration, parenteral administration (e.g., epifascial, intracapsular, intracutaneous, intradermal, intramuscular, intraorbital, intraperitoneal, intraspinal, intrasternal, intravascular, intravenous, parenchymatous, or subcutaneous administration), transdermal administration, and administration by osmotic pump. One preferred method of administration is parenteral administration, by intravenous or subcutaneous injection.

For oral administration, the formulation of the HAUSP modulator, protein, or nucleic acid may be presented as capsules, tablets, powders, granules, or as a suspension. The formulation may have conventional additives, such as lactose, mannitol, corn starch, or potato starch. The formulation also may be presented with binders, such as crystalline cellulose, cellulose derivatives, acacia, corn starch, or gelatins. Additionally, the formulation may be presented with disintegrators, such as corn starch, potato starch, or sodium carboxymethylcellulose. The formulation also may be presented with dibasic calcium phosphate anhydrous or sodium starch glycolate. Finally, the formulation may be presented with lubricants, such as talc or magnesium stearate.

For parenteral administration, the HAUSP modulator, protein, or nucleic acid may be combined with a sterile aqueous solution, which is preferably isotonic with the blood of the subject. Such a formulation may be prepared by dissolving a solid active ingredient in water containing physiologically-compatible substances, such as sodium chloride, glycine, and the like, and having a buffered pH compatible with physiological conditions, so as to produce an aqueous solution, then rendering said solution sterile. The formulation may be presented in unit or multi-dose containers, such as sealed ampules or vials. The formulation also may be delivered by any mode of injection, including any of those described above.

For transdermal administration, the HAUSP modulator, protein, or nucleic acid may be combined with skin penetration enhancers, such as propylene glycol, polyethylene glycol, isopropanol, ethanol, oleic acid, N-methylpyrrolidone, and the like, which increase the permeability of the skin to the modulator, protein, or nucleic acid, and permit the modulator, protein or nucleic acid to penetrate through the skin and into the bloodstream. The composition of enhancer and modulator, protein, or nucleic acid also may be further combined with a polymeric substance, such as ethylcellulose, hydroxypropyl cellulose, ethylene/vinylacetate, polyvinyl pyrrolidone, and the like, to provide the composition in gel form, which may be dissolved in solvent, such as methylene chloride, evaporated to the desired viscosity, and then applied to backing material to provide a patch. The modulator, protein, or nucleic acid may be administered transdermally, at or near the site on the subject where the neoplasm is localized. Alternatively, the modulator, protein, or nucleic acid may be administered transdermally at a site other than the affected area, in order to achieve systemic administration.

The HAUSP modulator, protein, or nucleic acid of the present invention also may be released or delivered from an osmotic mini-pump or other time-release device. The release rate from an elementary osmotic mini-pump may be modulated with a microporous, fast-response gel disposed in the release orifice. An osmotic mini-pump would be useful for controlling release, or targeting delivery, of the modulator, protein, or nucleic acid.

In accordance with the methods of the present invention, where the modulator of HAUSP expression is a protein, or where HAUSP protein is the therapeutic of choice, the protein may be administered to a subject by introducing to the subject the protein itself, or by introducing to the subject a nucleic acid encoding the protein in a manner permitting expression of the protein. Accordingly, in one embodiment of the present invention, activity of HAUSP in a subject may be increased by administering to the subject an amount of a protein (e.g., a modulator of HAUSP expression, or the HAUSP protein itself). In a further embodiment of the present invention, activity of HAUSP in the subject may be increased by administering to the subject a nucleic acid sequence encoding a protein (e.g., a modulator of HAUSP expression, or the HAUSP protein itself), in a manner permitting expression of HAUSP in the subject.

The proteins of the present invention may be administered or introduced to a subject by known techniques used for the introduction of proteins and other drugs, including, for example, injection and transfusion. Where a neoplasm is localized to a particular portion of the body of the subject, it may be desirable to introduce the therapeutic protein directly to that area by injection or by some other means (e.g., by introducing the protein into the blood or another body fluid). The amount of protein to be used is an amount effective to treat neoplasia in the subject, as defined above, and may be readily determined by the skilled artisan.

In the method of the present invention, where the modulator of HAUSP expression is a protein, or where HAUSP protein is the therapeutic of choice, the protein also may be administered or introduced to the subject by introducing into a sufficient number of cells of the subject a nucleic acid encoding the protein, in a manner permitting expression of the protein. The amount of nucleic acid encoding the therapeutic protein is an amount that will produce the protein in an amount effective to treat neoplasia, as defined above, in the subject. This amount may be readily determined by the skilled artisan.

Nucleic acid encoding the modulator of HAUSP expression, or the HAUSP protein, as well as any nucleotide modulators of HAUSP expression, all may be introduced to the subject using conventional procedures known in the art, including, without limitation, electroporation, DEAE Dextran transfection, calcium phosphate transfection, lipofection, monocationic liposome fusion, polycationic liposome fusion, protoplast fusion, creation of an in vivo electrical field, DNA-coated microprojectile bombardment, injection with recombinant replication-defective viruses, homologous recombination, in vivo gene therapy, ex vivo gene therapy, viral vectors, and naked DNA transfer, or any combination thereof. Recombinant viral vectors suitable for gene therapy include, but are not limited to, vectors derived from the genomes of viruses such as retrovirus, HSV, adenovirus, adeno-associated virus, Semiliki Forest virus, cytomegalovirus, and vaccinia virus.

It is within the confines of the present invention that a nucleic acid encoding a modulator of HAUSP expression, or the HAUSP protein itself, may be introduced into suitable cells in vitro, using conventional procedures, to achieve expression of the therapeutic protein in the cells. Cells expressing the modulator of HAUSP expression, or the HAUSP protein, then may be introduced into a subject to treat neoplasia in vivo. In such an ex vivo gene therapy approach, the cells are preferably removed from the subject, subjected to DNA techniques to incorporate nucleic acid encoding the therapeutic protein, and then reintroduced into the subject.

It is also within the confines of the present invention that a formulation containing a HAUSP modulator, protein, or nucleic acid may be further associated with a pharmaceutically-acceptable carrier, thereby comprising a pharmaceutical composition. Accordingly, the present invention further provides a pharmaceutical composition, comprising a modulator of HAUSP expression, or a HAUSP protein or a nucleic acid sequence encoding HAUSP, and a pharmaceutically-acceptable carrier. The pharmaceutically-acceptable carrier must be "acceptable" in the sense of being compatible with the other ingredients of the composition, and not deleterious to the recipient thereof. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc, and water, among others. Formulations of the pharmaceutical composition may be conveniently presented in unit dosage.

The formulations of the present invention may be prepared by methods well-known in the pharmaceutical arts. For example, the HAUSP modulator, protein, or nucleic acid may be brought into association with a carrier or diluent, as a suspension or solution. Optionally, one or more accessory ingredients (e.g., buffers, flavoring agents, surface active agents, and the like) also may be added. The choice of carrier will depend upon the route of administration. The pharmaceutical composition would be useful for administering the HAUSP modulator, protein, or nucleic acid of the present invention to a subject to treat neoplasia. The HAUSP modulator, protein, or nucleic acid is provided in an amount that is effective to treat neoplasia in a subject to whom the pharmaceutical composition is administered. That amount may be readily determined by the skilled artisan, as described above.

As disclosed herein, the inventors have determined, using mass-spectrometry analysis of affinity-purified p53-associated factors, that HAUSP interacts with p53. HAUSP strongly stabilizes p53, even in the presence of excess Mdm2, and induces p53-dependent cell-growth repression and apoptosis. Significantly, HAUSP has an intrinsic enzymatic activity that specifically deubiquitinates p53, both in vitro and in vivo. In contrast, expression of a catalytically-inactive HAUSP point mutant in cells increases the levels of p53 ubiquitination, and destabilizes p53. These findings reveal an important mechanism by which p53 can be stabilized by direct deubiquitination. In view of the foregoing, the present invention further provides a method for deubiquitinating p53 in a cell containing p53, comprising contacting the cell with HAUSP, in an amount effective to deubiquitinate p53.

The method of the present invention may be used to deubiquitinate p53, or remove ubiquitin from p53, in vitro, or in vivo in a subject. Deubiquitination of p53 may be detected by known procedures, including any of the methods, molecular procedures, and assays disclosed herein. The ability of HAUSP to modulate deubiquitination of p53 renders HAUSP particularly useful for treating neoplasias, particularly p53-associated neoplasias, as described above. Accordingly, in one embodiment of the present invention, the subject is a human with neoplasia.

HAUSP may be contacted with a cell containing p53 in vitro, or in vivo in a subject, by introducing HAUSP protein, or a nucleic acid sequence encoding HAUSP, to the cell, in a manner permitting expression of HAUSP. The cell may be contained in tissue of the subject, and may be detected in tissue of the subject by standard detection methods readily determined from the known art, examples of which include, without limitation, immunological techniques (e.g., immunohistochemical staining), fluorescence imaging techniques, and microscopic techniques. In one embodiment of the present invention, the contacting is effected in vivo in a subject by administering HAUSP to the subject. Methods and formulations for introducing or administering proteins and nucleic acid sequences to subjects have already been described.

The present invention also provides a method for identifying an agent that is reactive with p53, by assessing the ability of a candidate agent to inhibit HAUSP-p53 interaction. Unless otherwise indicated, "p53" includes both a p53 protein (GenBank Accession No. CAA38095), including conservative substitutions thereof, and a p53 analogue. A "p53 analogue" is a functional variant of the p53 protein, having p53 biological activity, that has 60% or greater (preferably, 70% or greater) amino-acid-sequence homology with the p53 protein. As further used herein, the term "p53 biological activity" refers to the activity of a protein or peptide that demonstrates detectable binding with HAUSP (i.e., binding of approximately two fold, or, more preferably, approximately five fold, above the background binding of a negative control), under the conditions of the assays described herein, although affinity may be different from that of p53.

The method of the present invention comprises the steps of: (a) contacting a candidate agent with p53, in the presence of HAUSP; and (b) assessing the ability of the candidate agent to inhibit HAUSP-p53 interaction. As used herein, an "agent" shall have the definition provided above, and shall include any examples of agents described above. An agent that binds to p53 may be either natural or synthetic. An agent that is reactive with p53, as disclosed herein, would have the ability to inhibit HAUSP-p53 interaction by binding to p53 in the place of HAUSP, thereby inhibiting the interaction of HAUSP and p53. A candidate agent having the ability to bind p53 would, as a consequence of this binding, either prevent p53 activity through steric hindrance, or mimic HAUSP in its deubiquitination of p53 and thereby reinforce the stabilizing power of HAUSP.

According to the method of the present invention, an agent that is reactive with p53 may be identified using an in vitro assay (e.g., direct binding assay, competitive binding assay, etc.). For instance, in a direct binding assay, the binding of a candidate agent to p53 or a peptide fragment thereof may be measured directly. The candidate agent may be supplied by a peptide library, for example.

Alternatively, in a competitive binding assay, standard methodologies may be used in order to assess the ability of a candidate agent to displace or replace HAUSP in its binding to p53, thereby inhibiting the interaction of HAUSP and p53. In such a competitive binding assay, the candidate agent competes with HAUSP for binding to p53, and, once bound to p53, may either sterically hinder binding of HAUSP to p53, thereby preventing deubiquitination of p53 by HAUSP, or function as HAUSP in deubiquitinating or otherwise stabilizing p53. A competitive binding assay represents a convenient way to assess inhibition of HAUSP-p53 interaction, since it allows the use of crude extracts containing p53 and HAUSP.

A competitive binding assay may be carried out by adding p53, or an extract containing p53 biological activity (as defined above), to a mixture containing the candidate agent and labeled HAUSP, both of which are present in the mixture in known concentrations. After incubation, the p53/agent complex may be separated from the unbound labeled HAUSP and unlabeled candidate agent, and counted. The concentration of the candidate agent required to inhibit 50% of the binding of the labeled HAUSP to p53 (IS) then may be calculated.

The binding assay formats described herein employ labeled assay components. Labeling of HAUSP or p53 may be accomplished using one of a variety of different chemiluminescent and radioactive labels known in the art, including any of those described above. Qualitative results then may be obtained by competitive autoradiographic-plate binding assays; alternatively, Scatchard plots may be used to generate quantitative results. The labels of the present invention may be coupled directly or indirectly to the desired component of the assay, according to methods well known in the art. The choice of label depends on a number of relevant factors, including the sensitivity required, the ease of conjugation with the compound to be labeled, stability requirements, and available instrumentation.

Both direct and competitive binding assays may be used in a variety of different configurations. In one competitive binding assay, for example, the candidate agent may compete against labeled HAUSP (the labeled analyte) for a specific binding site on p53 (the capture agent) that is bound to a solid substrate, such as a column chromatography matrix or tube.

Alternatively, the candidate agent may compete for a specific binding site on labeled p53 (the labeled analyte) against wild-type HAUSP or a fragment thereof (the capture agent) that is bound to a solid substrate. The capture agent is bound to the solid substrate in order to effect separation of bound labeled analyte from the unbound labeled analyte. In either type of competitive binding assay, the concentration of labeled analyte that binds the capture agent bound to the solid substrate is inversely proportional to the ability of a candidate agent to compete in the binding assay. The amount of inhibition of labeled analyte by the candidate agent depends on the binding assay conditions and on the concentrations of candidate agent, labeled analyte, and capture agent that are used.

Another competitive binding assay may be conducted in a liquid phase. In this type of assay, any of a variety of techniques known in the art may be used to separate the bound labeled analyte (which may be either HAUSP or p53) from the unbound labeled analyte. Following such separation, the amount of bound labeled analyte may be determined. The amount of unbound labeled analyte present in the separated sample is inversely proportional to the amount of bound labeled analyte.

In the further alternative, a homogeneous binding assay may be performed, in which a separation step is not needed. In this type of binding assay, the label on the labeled analyte (which may be either HAUSP or p53) is altered by the binding of the analyte to the capture agent. This alteration in the labeled analyte results in a decrease or increase in the signal emitted by the label, so that measurement of the label at the end of the binding assay allows for detection or quantification of the analyte.

Under specified assay conditions, a candidate agent is considered to be capable of inhibiting the binding of HAUSP to p53 in a competitive binding assay if the amount of binding of the labeled analyte to the capture agent is decreased by 50% (preferably 90%) or more. Where a direct binding assay configuration is used, a candidate agent is considered to bind p53 when the signal measured is twice the background level or higher. Furthermore, as proof of the specificity of the candidate agent identified using an HAUSP competitive binding assay, binding competition also may be performed using purified p53 in the presence of washed ribosomes.

The p53 tumor-suppressor is activated by numerous stressors to induce apoptosis, cell-cycle arrest, or senescence. p53-mediated biological activity is often the focus of research because, as described herein, p53 has a strong tumor-suppressor function. Nevertheless, p53 has also been implicated in other biological events. For example, in mice having a deletion mutation in the first six exons of the p53 gene—a mutation which confers phenotypes consistent with activated, rather than inactivated, p53—enhanced resistance to spontaneous tumors was accompanied by early onset of phenotypes associated with aging, including reduced longevity, osteoporosis, generalized organ atrophy, and a diminished stress tolerance. These data suggest that p53 has a role in regulating aging in an organism (Tyner et al., p53 mutant mice that display early ageing-associated phenotypes. *Nature*, 415: 45-53, 2002).

Additionally, it has been suggested that p53 plays a role in generating side-effects relating to usage of chemotherapeutics. Anticancer drugs stimulate apoptosis in hair follicles (HF), and cause hair loss—the most common side-effect of chemotherapy. In one mouse model for chemotherapy-induced hair loss, it was demonstrated that p53 is essential for this process. Specifically, in contrast to wild-type mice, p53-deficient mice displayed neither hair loss nor apoptosis in HF keratinocytes that maintained active proliferation after cyclophosphamide treatment. These observations indicate that local pharmacological inhibition of p53 may be useful to prevent chemotherapy-associated hair loss (Botchkarev et al., p53 is essential for chemotherapy-induced hair loss. *Cancer Res.*, 60:5002-02, 2000).

In view of the foregoing, it is clear that therapeutics designed around, or similar to, the structure of HAUSP may be useful in treating a number of conditions associated with p53, including neoplasia, aging, and chemotherapeutic-induced or drug-induced side effects. Thus, once the candidate agent of the present invention has been screened, and has been determined to have suitable binding affinity to p53 (i.e., it is reactive with p53), it may be evaluated to ascertain whether it has an effect on biological events or processes in which p53 has been implicated, including neoplasia, aging, and side-effects associated with usage of pharmaceuticals and other chemotherapeutics. In particular, the candidate agent may be assessed for its ability to act as an inhibitor to cell division or to otherwise function as an appropriate tumor-suppressing agent. It is expected that the candidate agent of the present invention will be useful to treat neoplasias, including those disclosed herein. The candidate agent also may be assessed for its ability to attenuate adverse effects associated with aging, or adverse effects associated with administration of a chemotherapeutic to a subject.

Accordingly, the present invention further comprises the steps of: (c) contacting the candidate agent with one or more cells containing p53; and (d) determining if the agent has an effect on one or more p53-associated biological events in the one or more cells. As used herein, a "p53-associated biological event" includes a biochemical or physiological process in which p53 activity has been implicated. As disclosed herein, examples of p53-associated biological events include p53-associated neoplasia, adverse effects associated with the aging process (e.g., diminished stress tolerance, generalized organ atrophy, osteoporosis, and reduced longevity), and adverse side-effects associated with administration or use of pharmaceuticals and other chermotherapeutics (e.g., alopecia, or hair loss, and nausea).

In one embodiment of the present invention, for example, the method may further comprise the steps of: (c) contacting the candidate agent with one or more cells of a neoplasm ("neoplastic cells"); and (d) determining if the agent has an effect on proliferation of the neoplastic cells. As used herein, "proliferation" includes, without limitation, division, growth, and multiplication of neoplastic cells. Examples of neoplastic cells with which the candidate agent may be contacted include human lung carcinoma cells (H1299) and any other neoplastic cells containing p53. As further used herein, a cell "containing p53" is a cell in which p53, or a derivative or homologue thereof, is naturally expressed or naturally occurs. According to this method of the present invention, a candidate agent may be contacted with neoplastic cells in vitro. For example, a culture of neoplastic cells may be incubated with a preparation containing the candidate agent. The candidate agent's effect on proliferation of the neoplastic cells then may be assessed by any biological assays or methods known in the art, including histological analysis.

The present invention is further directed to agents identified by the above-described identification methods. Such agents may be useful for treating a p53-associated conditions. As used herein, a "p53-associated condition" is a condition, disease, or disorder in which p53 activity has been implicated, and includes the following: p53-associated neoplasia in a subject in need of treatment, adverse effects associated with aging in a subject in need of treatment, and adverse side-effects associated with use of a pharmaceutical or chemotherapeutic in a subject. The p53-associated condition may be treated in the subject by administering to the subject an amount of the agent effective to treat the p53-associated condition in the subject. This amount may be readily determined by one skilled in the art.

The present invention also provides a pharmaceutical composition comprising the agent identified by the above-described identification method and a pharmaceutically-acceptable carrier. Examples of suitable pharmaceutically-acceptable carriers, and methods of preparing pharmaceutical formulations and compositions, are described above. The pharmaceutical composition of the present invention would be useful for administering to a subject an agent that is reactive with p53, in order to treat a p53-associated condition. In such cases, the pharmaceutical composition is administered to a subject in an amount effective to treat the p53-associated condition.

The present invention also provides a complex comprising HAUSP and p53. In such a HAUSP-p53 complex, amino acid residues of a p53-binding site of HAUSP are in direct van der Waal and/or hydrogen bond and/or salt-bridge contact with the amino acid residues of p53. The complex of the present invention may comprise the full amino acid sequence of HAUSP complexed with the full amino acid sequence of p53. In another embodiment, the complex of the present invention comprises at least the N-terminus domain of HAUSP, which contains a p53-binding site of HAUSP.

As used herein, the "N-terminus domain of HAUSP" means residues 1-248 of HAUSP, as well as analogues thereof. Moreover, as used herein, a "binding site" refers to a region of a molecule or molecular complex that, as a result of its shape and charge potential, favorably interacts or associates with another agent—including, without limitation, a protein, polypeptide, peptide, nucleic acid (including DNA or RNA), molecule, compound, antibiotic, or drug—via various covalent and/or non-covalent binding forces. Accordingly, as contemplated by the present invention, a "p53-binding site of HAUSP" is a binding site on HAUSP that, as a result of its shape, reactivity, charge, potential, and other characteristics, favorably interacts or associates with another agent, including, without limitation, a protein (e.g., p53), polypeptide, peptide, nucleic acid (e.g., DNA or RNA), molecule, compound, antibiotic, or drug.

It will be obvious to the skilled practitioner that the numbering of any amino acid residues in the various isoforms of HAUSP, or in HAUSP analogues covered by the present invention, may be different than that set forth herein, or may contain certain conservative amino acid substitutions that produce the same p53-binding activity as that described herein. Corresponding amino acids and conservative substitutions in other isoforms or analogues are easily identified by visually inspecting the relevant amino acid sequences, or by using commercially-available homology software programs.

A p53-binding site of HAUSP may include the actual site on HAUSP of p53 binding. A p53-binding site also may include accessory binding sites on HAUSP, adjacent or proximal to the actual site of p53 binding, that nonetheless may affect HAUSP or p53-HAUSP activity upon interaction or association with a particular agent—either by direct interference with the actual site of p53 binding, or by indirectly affecting the steric conformation or charge potential of the HAUSP molecule, and thereby preventing or reducing p53 binding to HAUSP at the actual site of p53 binding.

Identification of a binding site of a molecule or molecular complex is important because the biological activity of the molecule or molecular complex frequently results from interaction between an agent/ligand and one or more binding sites of the molecule or molecular complex. Therefore, localization of a p53-binding site of HAUSP provides the most suitable tool for identifying inhibitors that affect the activity of HAUSP or HAUSP-p53. Localization of a p53-binding site of HAUSP also permits the use of various molecular design and analysis techniques for the purpose of designing and synthesizing chemical agents capable of favorably associating or interacting with a p53-binding site of HAUSP or a HAUSP analogue, wherein said chemical agents potentially act as inhibitors of HAUSP or HAUSP-p53 activity. In view of the foregoing, the HAUSP-p53 interaction and the HAUSP-p53 complex of the present invention may be used as tools in the rational design and development of drug screens, as a target for small-molecule inhibitors that can act as inhibitor agents or modulators, and as a basis for peptidomimetics.

The present invention further provides a point-mutant HAUSP protein (HAUSP-cs), in which a highly conserved Cys residue at the core domain is replaced by Ser. More particularly, the point-mutant protein comprises the amino acid sequence set forth in FIG. 6 (SEQ ID NO:6), in which Ser is substituted for Cys at amino acid residue 223. This mutant protein retains its strong binding with p53 in vitro. Additionally, as disclosed herein, expression of HAUSP-cs in cells increased the level of p53 ubiquitination, indicating that HAUSP-cs may function as a dominant-negative mutant by interfering with endogenous HAUSP-mediated deubiquitination of p53. Also provided herein are a nucleic acid sequence encoding the HAUSP point-mutant protein of the present invention, and a cell transfected with the nucleic acid sequence.

The present invention further provides a non-human transgenic animal that expresses either reduced, mutant, or no HAUSP gene products, or that expresses only human HAUSP gene products. In particular, the present invention provides a transgenic non-human animal in which HAUSP has been selectively inactivated. More specifically, the present invention provides a transgenic non-human animal whose genome comprises a disruption in the HAUSP gene, wherein the transgenic animal exhibits a decreased level of functional HAUSP protein relative to wild-type. The non-human animal may be any suitable animal (e.g., cat, cattle, dog, horse, goat, rodent, and sheep), but is preferably a rodent. More preferably, the non-human animal is a rat or a mouse.

Unless otherwise indicated, the term "HAUSP gene" refers herein to a nucleic acid sequence encoding HAUSP protein, and any allelic variants thereof. Due to the degeneracy of the genetic code, the HAUSP gene of the present invention includes a multitude of nucleic acid substitutions that will also encode HAUSP protein. An "endogenous" HAUSP gene is one that originates or arises naturally, from within an organism. The terms "HAUSP protein", "HAUSP analogue", and "HAUSP-protein biological activity" have been defined above.

As used herein, the term "transgenic non-human animal" refers to a genetically-engineered non-human animal, produced by experimental manipulation, whose genome has been altered by introduction of a transgene. As further used herein, the term "transgene" refers to a nucleic acid (e.g., DNA or a gene) that has been introduced into the genome of an animal by experimental manipulation, wherein the introduced gene is not endogenous to the animal, or is a modified or mutated form of a gene that is endogenous to the animal. The modified or mutated form of an endogenous gene may be produced through human intervention (e.g., by introduction of a point mutation, introduction of a frameshift mutation, deletion of a portion or fragment of the endogenous gene, insertion of a selectable marker gene, insertion of a termination codon, etc.). A transgenic non-human animal may be produced by several methods involving human intervention, including, without limitation, introduction of a transgene into an embryonic stem cell, newly fertilized egg, or early embryo of a non-human animal; integration of a transgene into a chromosome of the somatic and/or germ cells of a non-human animal; and any of the methods described herein.

The transgenic animal of the present invention has a genome in which the HAUSP gene has been selectively inactivated, resulting in a disruption in its endogenous HAUSP gene. As used herein, a "disruption" refers to a mutation (i.e., a permanent, transmissible change in genetic material) in the HAUSP gene that prevents normal expression of functional HAUSP protein (e.g., it results in expression of a mutant HAUSP protein; it prevents expression of a normal amount of HAUSP protein; or it prevents expression of HAUSP protein). Examples of a disruption include, without limitation, a point mutation, introduction of a frameshift mutation, deletion of a portion or fragment of the endogenous gene, insertion of a selectable marker gene, and insertion of a termination codon. As used herein, the term "mutant" refers to a gene (or its gene product) which exhibits at least one modification in its sequence (or its functional properties) as compared with the wild-type gene (or its gene product). In contrast, the term "wild-type" refers to the characteristic genotype (or phenotype) for a particular gene (or its gene product), as found most frequently in its natural source (e.g., in a natural population). A wild-type animal, for example, expresses functional HAUSP.

Selective inactivation in the transgenic non-human animal of the present invention may be achieved by a variety of methods, and may result in either a heterozygous disruption (wherein one HAUSP gene allele is disrupted, such that the resulting transgenic animal is heterozygous for the mutation) or a homozygous disruption (wherein both HAUSP gene alleles are disrupted, such that the resulting transgenic animal is homozygous for the mutation). In one embodiment of the present invention, the endogenous HAUSP gene of the transgenic animal is disrupted through homologous recombination with a nucleic acid sequence that encodes a region common to HAUSP gene products. By way of example, the disruption through homologous recombination may generate a knockout mutation in the HAUSP gene, particularly a knockout mutation wherein at least one deletion has been introduced into at least one exon of the HAUSP gene (e.g., exon 1).

Additionally, in accordance with the methods of the present invention, a disruption in the HAUSP gene may result from insertion of a heterologous selectable marker gene into the endogenous HAUSP gene. As used herein, the term "selectable marker gene" refers to a gene encoding an enzyme that confers upon the cell or organism in which it is expressed a resistance to a drug or antibiotic, such that expression or activity of the marker can be selected for (e.g., a positive marker, such as the neo gene) or against (e.g., a negative marker, such as the dt gene). As further used herein, the term "heterologous selectable marker gene" refers to a selectable marker gene that, through experimental manipulation, has been inserted into the genome of an animal in which it would not normally be found. Such a heterologous selectable marker gene may be inserted into any coding exon of the HAUSP gene.

The transgenic non-human animal of the present invention exhibits decreased expression of functional HAUSP protein relative to a corresponding wild-type non-human animal of the same species. As used herein, the phrase "exhibits decreased expression of functional HAUSP protein" refers to a transgenic animal in whom the detected amount of functional HAUSP is less than that which is detected in a corresponding animal of the same species whose genome contains a wild-type HAUSP gene. Preferably, the transgenic animal contains at least 50% less functional HAUSP than the corresponding wild-type animal. More preferably, the transgenic animal contains at least 75% less functional HAUSP than the corresponding wild-type animal. Even more preferably, the transgenic animal contains at least 90% less functional HAUSP than the corresponding wild-type animal. Levels of HAUSP in an animal, as well as HAUSP activity, may be detected using standard assays such as those known in the art.

Accordingly, where the transgenic animal of the present invention exhibits decreased expression of functional HAUSP protein relative to wild-type, the level of functional HAUSP protein in the transgenic animal is lower than that which otherwise would be found in nature. In one embodiment of the present invention, the transgenic animal expresses mutant HAUSP (regardless of amount). In another embodiment of the present invention, the transgenic animal expresses no HAUSP (wild-type or mutant). In yet another embodiment of the present invention, the transgenic animal expresses wild-type HAUSP protein, but at a decreased level of expression relative to a corresponding wild-type animal of the same species.

The transgenic non-human animal of the present invention, or any transgenic non-human animal exhibiting decreased expression of functional HAUSP protein relative to wild-type, may be produced by a variety of techniques for genetically engineering transgenic animals. For example, to create a transgenic non-human animal exhibiting decreased expression of functional HAUSP protein relative to a corresponding wild-type animal of the same species, a HAUSP targeting vector first may be generated, using techniques well-known in the art.

As used herein, the term "HAUSP targeting vector" refers to an oligonucleotide sequence that comprises a portion, or all, of the HAUSP gene, and is sufficient to permit homologous recombination of the targeting vector into at least one allele of the endogenous HAUSP gene within the recipient cell. In one embodiment of the present invention, the targeting vector further comprises a positive or negative heterologous selectable marker gene (e.g., the positive selection gene, neo). Additionally, the targeting vector may be a replacement vector (i.e., the selectable marker gene replaces an endogenous target gene). For example, the replacement vector of the present invention may insert a heterologous selectable marker gene into the HAUSP gene, resulting in a disruption of the HAUSP gene such that functional HAUSP protein is not expressed. Such a disruption is referred to herein as a "null" or "knockout" mutation. It is also within the scope of the present invention that the targeting vector may be an insertion vector. By way of example, the HAUSP targeting vector of the present invention may be an oligonucleotide sequence comprising at least a portion of a non-human HAUSP gene in which there is at least one deletion in at least one exon (e.g., exon 1 of HAUSP).

In the method of the present invention, the HAUSP targeting vector that has been generated may be introduced into a recipient cell (comprising a wild-type HAUSP gene) of a non-human animal, to produce a treated recipient cell. This introduction may be performed under conditions suitable for homologous recombination of the vector into at least one of the wild-type HAUSP genes in the genome of the recipient cell. The recipient cell may be, for example, an embryonic stem cell, or a cell of an oocyte or zygote.

The HAUSP targeting vector of the present invention may be introduced into the recipient cell by any in vivo or ex vivo means suitable for gene transfer, including, without limitation, electroporation, DEAE Dextran transfection, calcium phosphate transfection, lipofection, monocationic liposome fusion, polycationic liposome fusion, protoplast fusion, creation of an in vivo electrical field, DNA-coated microprojectile bombardment, injection with recombinant replication-defective viruses, homologous recombination, viral vectors, and naked DNA transfer, or any combination thereof. Recombinant viral vectors suitable for gene transfer include, but are not limited to, vectors derived from the genomes of viruses such as retrovirus, HSV, adenovirus, adeno-associated virus, Semiliki Forest virus, cytomegalovirus, and vaccinia virus.

In accordance with the methods of the present invention, the treated recipient cell then may be introduced into a blastocyst of a non-human animal of the same species (e.g., by injection or microinjection into the blastocoel cavity), to produce a treated blastocyst. Thereafter, the treated blastocyst may be introduced (e.g., by transplantation) into a pseudopregnant non-human animal of the same species, for expression and subsequent germline transmission to progeny. For example, the treated blastocyst may be allowed to develop to term, thereby permitting the pseudopregnant animal to deliver progeny comprising the homologously-recombined vector, wherein the progeny may exhibit decreased expression of HAUSP relative to corresponding wild-type animals of the same species. It then may be possible to identify a transgenic non-human animal whose genome comprises a disruption in its endogenous HAUSP gene. The identified transgenic animal then may be interbred with other founder transgenic animals, to produce heterozygous or homozygous non-human animals exhibiting decreased expression of functional HAUSP protein relative to corresponding wild-type animals of the same species. The present invention further provides a transgenic non-human animal created by the above-described method.

As discussed above, studies to date suggest that the p53 pathway is dysfunctional in most, if not all, cases of cancer, and that p53 itself is mutated in approximately 60% of all cancers. In cancer cases where wild-type p53 is detected, then, it is believed that p53 cannot be activated or stabilized because another enzyme or biochemical in the p53 pathway (e.g., HAUSP) is defective. Studies on the transgenic non-human animal of the present invention, which exhibits decreased expression of functional HAUSP protein relative to wild-type, and which lacks the wild-type HAUSP gene, may facilitate an understanding of the physiological role of HAUSP in tumorigenesis, particularly in p53-associated neoplasias. For example, the transgenic non-human animal could be used to test whether loss of HAUSP affects the development of neoplasias. A transgenic non-human animal genetically engineered to express human HAUSP also will be a valuable reagent for testing lead HAUSP compounds in vivo. Moreover, the inventors' transgenic non-human animal provides a valuable, unique, and useful reagent for screening for modulators of p53 activity that could replace HAUSP in its interaction with p53.

The present invention is described in the following Examples, which are set forth to aid in the understanding of the invention, and should not be construed to limit in any way the scope of the invention as defined in the claims which follow thereafter.

EXAMPLE 1

1. Introduction

The p53 tumor suppressor is a short-lived protein that is maintained at low levels in normal cells by Mdm2-mediated ubiquitination and subsequent proteolysis (Ashcroft and Vousden, Regulation of p53 stability. *Oncogene,* 18:7637-43, 1999; Oren, M., Regulation of the p53 tumor suppressor protein. *J. Biol. Chem.,* 274, 36031-034, 1999; Freedman et al., Functions of the MDM2 oncoprotein. *Cell Mol. Life Sci.,* 55:96-107, 1999). Stabilization of p53 is critical for its tumor-suppressor function (Ashcroft and Vousden, supra; Oren, M., supra; Freedman et al., supra; Prives and Hall, The p53 pathway. *J. Pathol.,* 187:112-26, 1999; Vogelstein et al., Surfing the p53 network. *Nature,* 408:307-10, 2000). However, the precise mechanism by which ubiquitinated p53 levels are regulated in vivo is not completely understood.

By mass spectrometry of affinity-purified p53-associated factors, the inventors have identified HAUSP (herpesvirus-associated ubiquitin-specific protease) (Everett et al., A novel ubiquitin-specific protease is dynamically associated with the PML nuclear domain and binds to a herpesvirus regulatory protein. *EMBO J.,* 16:566-77, 1997) as a p53-interacting protein. HAUSP strongly stabilizes p53, even in the presence of excess Mdm2, and induces p53-dependent cell-growth repression and apoptosis. Significantly, HAUSP has an intrinsic enzymatic activity that specifically deubiquitinates p53, both in vitro and in vivo. In contrast, expression of a catalytically-inactive HAUSP point mutant in cells increases the levels of p53 ubiquitination, and destabilizes p53. These findings reveal an important mechanism by which p53 can be stabilized by direct deubiquitination, and also implicate HAUSP as a tumor-suppressor in vivo, through stabilization of p53.

2. Materials and Methods a) Plasmids and Antibodies

To construct the HAUSP and USP11 expression vectors, the DNA sequences corresponding to the full-length proteins (Everett et al., supra; Chung and Baek, supra) were amplified by PCR from Marathon-Ready Hela cDNA (Clontech), and subcloned either into a pcDNA3-Topo vector (Invitrogen), or with a Flag-tag into either a pET-11 vector for expression in bacteria or a pCIN4 vector and pBabe vector for expression in mammalian cells (Luo et al, 2000, supra; Luo et al., Negative control of p53 by Sir2α promotes cell survival under stress. *Cell,* 107:137-48, 2001). Regarding the different deletion-mutant constructs, DNA sequences corresponding to different regions were amplified by PCR from the above constructs, and subcloned into respective expression vectors. To prepare the HAUSP antibody, inventors made a polyclonal antibody against the recombinant HAUSP full-length protein. The DNA sequence corresponding to the full-length protein was subcloned into the pET-15-His vector (Novagene). α-HAUSP antisera were raised in rabbits against the purified His-HAUSP protein (Covance), and further affinity-purified on a protein-A column.

b) Identification of HAUSP as a p53-Binding Protein

Elimination of non-specific protein binding is critical for successful identification of a bona fide binding partner for p53 in an affinity chromatography assay (Gu et al., supra; Luo et al, 2000, supra). Regarding this issue, the salt-concentration range between binding and elution conditions has been modified, as compared with the previous method (Gu et al., supra; Luo et al., 2000, supra) (e.g., 200 mM NaCl for binding, 500 mM NaCl for elution) to limit the number of proteins from the elution. Furthermore, nuclear extracts were extensively pre-cleaned with the GST column before loading on the GST-p53-affinity column. The mock purification was simultaneously performed on both the GST column loaded with the same nuclear extract, and an additional GST-p53 column loaded with a blank buffer for identifying any possible non-specific binding.

In brief, a column, which contains 40 µl of indicated GST-fusion-protein-coupled beads, was washed extensively with BC500 (25 mM Tris, 500 mM NaCl, 1 mM EDTA, 1 mM DTT, 10% glycerol, 0.2% NP40, 1% Triton X-100, 0.1% DOC, pH 7.8), and then equilibrated with BC200 (25 mM Tris, 200 mM NaCl, 1 mM EDTA, 1 mM DTT, 10% glycerol, 0.2% NP40, pH 7.8) for loading. Human lung carcinoma cells (H1299) were expanded in DMEM medium, and nuclear extracts were prepared essentially as previously described (Gu et al., supra; Luo et al., 2000, supra). Nuclear extracts were adjusted to 200 mM NaCl and 0.2% NP40, and pre-cleaned by flowing through the GST column for at least three times. 800 µl of the pre-cleaned nuclear extract was loaded on either the GST or GST-p53 mini-column. After washing with 1 ml of the BC200 buffer for five times, the associated proteins were eluted from column with 40 µl of BC500. The nuclear extract derived from about 10×10$^9$ cells was used for the large preparation.

c) Stabilization of p53 and Detecting Ubiquitination Levels of p53

The p53-null H1299 cells were transfected with 0.1-2 mg of CMV-Flag-p53, 2 mg of CMV-Mdm2, 1 mg of CMV-GFP, and 5-16 mg of either CMV-HAUSP or an expression vector for the indicated HAUSP mutant or other proteins. 24 h after the transfection, the cells were lysed in a Flag-lysis buffer (50 mM Tris, 137 mM NaCl, 10 mM NaF, 1 mM EDTA, 1% Triton X-100, 0.2% Sarkosyl, 1 mM DTT, 10% glycerol, pH 7.8; and fresh proteinase inhibitors) for Western blot analysis. The levels of GFP were detected with the anti-GFP monoclonal antibody (JL-8, Clontech) as a transfection-efficiency control. The ubiquitination levels of p53 were detected essentially as previously described (Rodriguez et al., Multiple C-terminal lysine residues target p53 for ubiquitin-proteasome-mediated degradation. *Mol. Cell. Biol.*, 20:8458-67, 2000). The cells were treated with 50 mM of a proteasome inhibitor, LLNL (Sigma), for 4 h before harvesting, and the cells were lysed in the Flag-lysis buffer with mild sonication. The cell extracts were immunoprecipitated with the Flag monoclonal antibody (M2), and subsequently resolved by either 8% or 4-20% SDS-PAGE gel (Novex), and analyzed by Western blot with a-p53 (DO-1).

For preparing a large amount of ubiquitinated p53 as the substrate for in vitro deubiquitination assay, the H1299 cells (5×10$^7$) were cotransfected with the Flag-p53 and Mdm2 expression vectors. After the same treatment as above, the ubiquitinated p53 was purified from the cell extracts on the M2-affinity column with the Flag-lysis buffer. After extensive washing with the Flag-lysis buffer, the proteins were eluted in a BC100 buffer (25 mM Tris, 100 mM NaCl, pH 7.8) with Flag-peptides (Sigma). The recombinant Flag-HAUSP and the mutant form (HAUSP-cs) were expressed in BL21 cells, and purified on the M2 column. For the in vitro deubiquitination assay reaction, the ubiquitinated p53 protein was incubated with the recombinant HAUSP (100 ng) or the same amount of other indicated proteins in a deubiquitination buffer (50 mM Tris-HCl, pH 8.0; 50 mM NaCl, 1 mM EDTA, 10 mM DTT, 5% glycerol) for 2 h at 37° C.

3. Results

By using a biochemical purification method with GST-p53 affinity chromatography (Gu et al., Synergistic activation of transcription by CBP and p53. Nature, 387:819-23, 1997; Luo et al, Deacetylation of p53 modulates its effect on cell growth and apoptosis. *Nature*, 408:377-81, 2000), the inventors have identified a p53-binding protein from nuclear extracts of human lung carcinoma cells (H1299). As indicated in FIG. 1A, there are a number of proteins present in the fractions eluted from the GST-p53 affinity column and from other columns. Strikingly, only one protein, p135 (relative molecular mass ~135,000; Mr: 135K), was specifically present in the associated factors obtained from the GST-p53 column, but was not present in the factors obtained from either the GST column or the control column (lane 3 vs. lanes 1, 2). Following a large preparation, enough material of the p135 band was obtained for mass spectrometry, and a total of five peptide sequences were obtained (SEQ ID NOs: 1-5). All five peptide sequences were derived from the herpesvirus protein Vmw110-associated cellular factor, known as HAUSP or human USP7 (Everett et al., A novel ubiquitin-specific protease is dynamically associated with the PML nuclear domain and binds to a herpesvirus regulatory protein. *EMBO J.,* 16:566-77, 1997).

Figure 9:
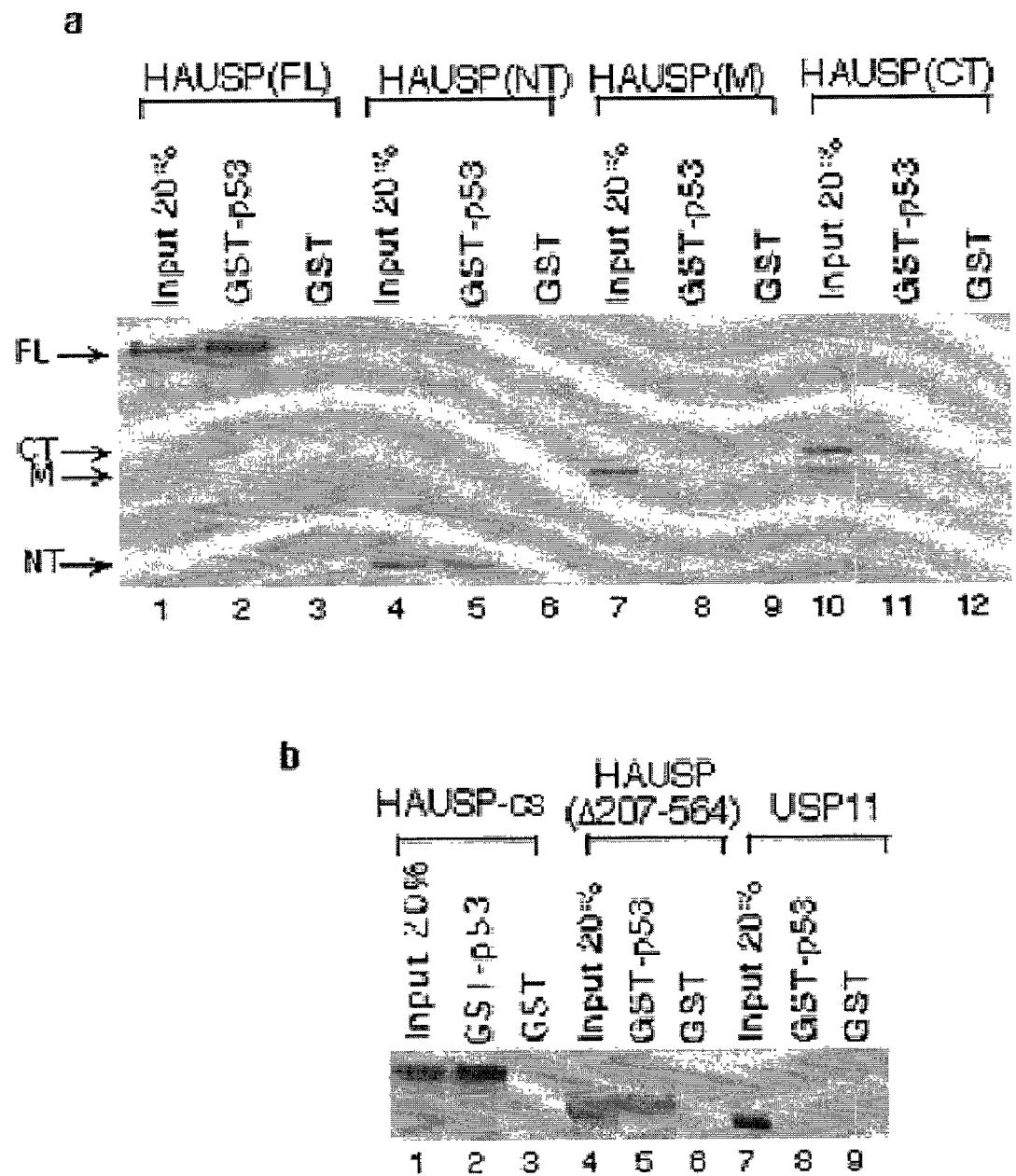

HAUSP belongs to the ubiquitin-(Ub)-specific processing protease (UBP) family of deubiquitination enzymes (DUBs), and contains the characteristic Cys and His motifs at the core enzymatic domain (Everett et al., supra). Interestingly, the amino-terminal and carboxyl-terminal extensions of HAUSP which have no significant homology to other members of the UBP family, and which are thought to be critical for the substrate specificity (Everett et al., supra; D'Andrea and Pellman, Deubiquitinating enzymes: a new class of biological regulators. *Crit. Rev. Biochem. Mol. Biol.,* 35:337-52, 1998; Chung and Baek, Deubiquitinating enzymes: their diversity and emerging roles. *Biochem. Biophys. Res. Commun.,* 266: 633-40, 1999; Wilkinson, K. D., Ubiquitination and deubiquitination: targeting of proteins for degradation by the proteasome. *Semin. Cell Dev. Biol.,* 11:141-48, 2000), directly bind to p53 in vitro. However, as shown in FIG. 9, $^{35}$S-labeled in vitro-translated HAUSP bound strongly to GST-p53, but not to GST alone (lane 2 vs. 3). Moreover, p53 bound tightly to the N-terminal extension [HAUSP(NT)] of HAUSP (lane 2, FIG. 9B), bound weakly to its carboxyl-terminal extension [HAUSP(CT)] (lane 8, FIG. 9B), but did not bind to the core catalytic domain [HAUSP(M)] (lane 5, FIG. 9B).

To evaluate in vivo interactions by co-immunoprecipitation analysis, p53-null cells (H1299) were transfected with p53 and a Flag-tagged HAUSP expression vector. As shown in FIG. 1B, p53 was readily immunoprecipitated from the cells cotransfected with both Flag-HAUSP and p53 (lane 4), but not from cells transfected with p53 alone (lane 2).

By using the HAUSP-specific antibody, the inventors also examined the interaction between the endogenous p53 and HAUSP proteins. Western blot analysis showed that p53 was present in the α-HAUSP immunoprecipitates from cell extracts of human lung carcinoma cells (H460), but not in the control immunoprecipitates obtained with the preimmnune serum (FIG. 1C). Interestingly, this interaction was strongly detected in cells subjected to genotoxic stress (lane 2 vs. lane 3, FIG. 1C), whereas only a slight enhancement was detected in the cells treated with a proteasome inhibitor, LLNL (lane 4, FIG. 1C). These results indicate that p53 interacts with HAUSP in vivo, and that the possible regulation of p53 by HAUSP may still be effective in the cells during the DNA damage response.

Figure 2:
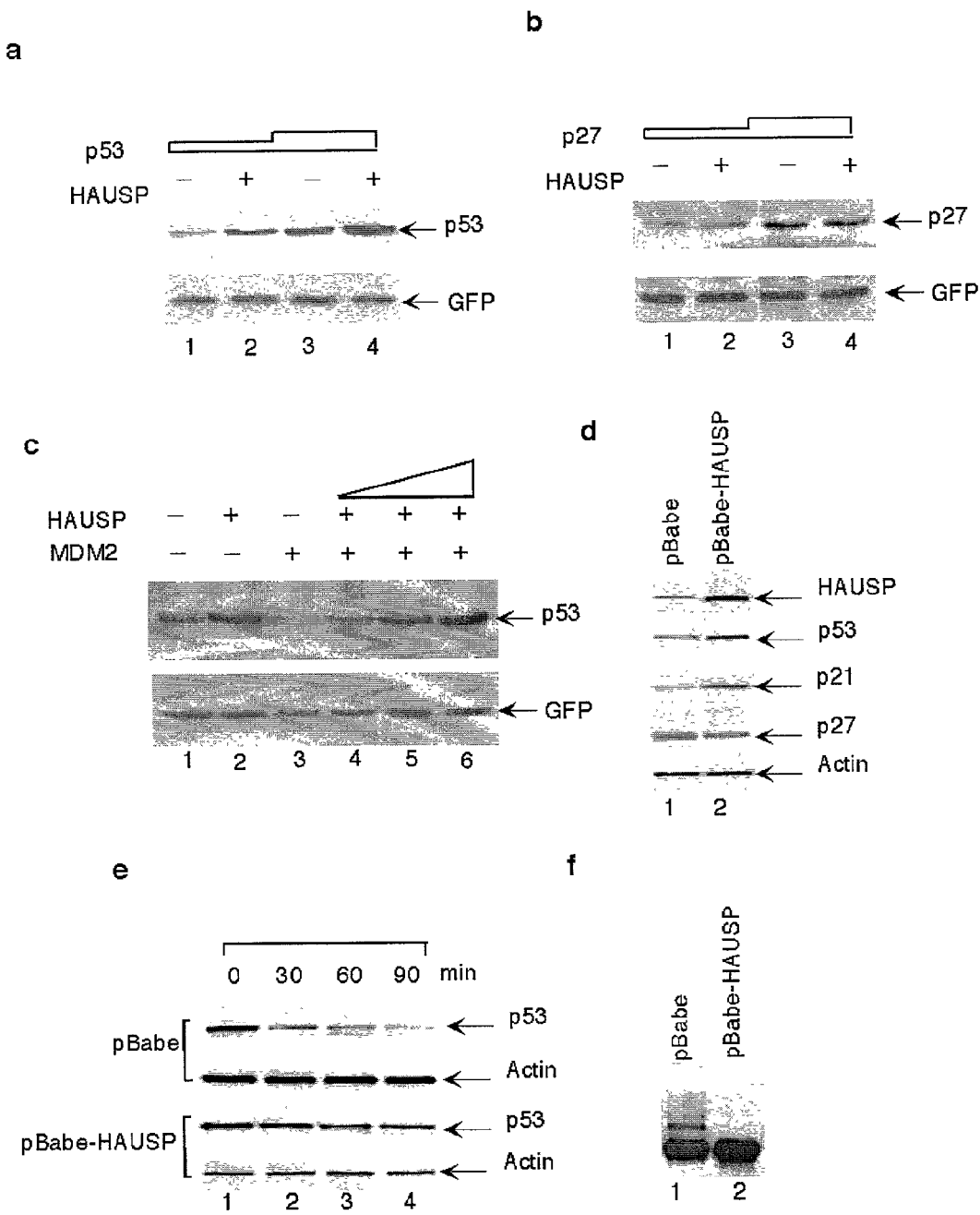

To determine the functional consequence of the p53-HAUSP interaction, the inventors tested whether HAUSP affects stabilization of p53. As indicated in FIG. 2A, HAUSP expression significantly increased the steady-state cellular levels of p53. In contrast, HAUSP had no obvious effect on the levels of p27 (FIG. 2B), another short-lived tumor-suppressor protein the stability of which is also regulated by the ubiquitination pathway (Slingerland and Pagano, Regulation of the cdk inhibitor p27 and its deregulation in cancer. *J. Cell Physi.*, 183:10-17, 2000). Moreover, as shown in FIG. 2C, HAUSP effectively rescues p53 from Mdm2-mediated degradation. Thus, although overexpression of Mdm2 significantly induced p53 degradation (lane 3 vs. 1, FIG. 2C), degradation of p53 was inhibited in a dose-dependent manner upon expression of HAUSP (lanes 4-6, FIG. 2C).

The inventors further examined the effect of HAUSP expression on stabilization of endogenous p53. Normal human fibroblast IMR-90 cells were infected with either a pBabe retrovirus empty vector or a pBabe retrovirus containing HAUSP. The inventors first examined the protein levels of endogenous p53 by Western blot analysis. Significantly higher levels of p53 proteins were detected in the pBabe-HAUSP-infected cells (lane 2 vs. 1, FIG. 2D). Interestingly, expression of endogenous p21 was also induced (lane 2 vs. 1, FIG. 2D), consistent with transient transfection results (data not shown), thereby indicating that HAUSP also activates p53-dependent transcriptional activation. In contrast, the levels of endogenous p27 remained the same, supporting the notion that HAUSP stabilizes p53, but not p27, in vivo. Notably, the half-life of p53 in the pBabe-HAUSP-infected cells was significantly increased by HAUSP expression (from about 20 min to about 90 min), whereas the half-life of p53 in the mock-infected cells was less than 30 min (FIG. 2E). To corroborate these results, inventors also found that the ubiquitination levels of p53 in the pBabe-HAUSP infected cells were reduced as compared with the levels in the mock-infected cells (FIG. 2F). Thus, these data demonstrate that HAUSP specifically stabilizes p53 in vivo.

To investigate the biological role of HAUSP, the inventors examined the effect of HAUSP on cell growth in a colony-formation assay. A pair of human lung carcinoma cells (H1299 and H460) were infected with either an empty pBabe-puro control retrovirus or a pBabe-puro retrovirus encoding HAUSP, and cultured for 2 weeks under pharmacological selection. Strikingly, HAUSP strongly inhibited cell growth of H460 cells, which express wild-type p53, but had no significant effect on p53-null H1299 cells (FIG. 3A). Similar cell growth repression by HAUSP was also observed in MEF p53 (+/+) cells, but not in MEF p53 (−/−) cells (FIG. 3A), suggesting that cell-growth repression by HAUSP is p53-dependent.

The inventors also tested whether HAUSP directly affects p53-dependent apoptosis. H1299 cells were transfected with p53 alone, or cotransfected with p53 and Mdm2, or with p53, Mdm2 and HAUSP. After transfection, the cells were fixed, stained for p53, and analyzed for apoptotic cells (SubG1) according to DNA content (Luo et al., supra). As indicated in FIG. 3B, although overexpression of p53 alone induced significant apoptosis (31.0%), Mdm2 strongly reduced the level of p53-dependent apoptosis (11.2%). However, expression of HAUSP effectively attenuated the inhibitory effect of Mdm2 on p53-mediated apoptosis (28.5% vs. 11.2%, FIG. 3B). These data demonstrate that HAUSP is critically involved in the regulation of p53-dependent apoptosis, as well as cell growth inhibition.

To elucidate the molecular mechanism by which HAUSP stabilizes p53, the inventors tested whether HAUSP directly controls the levels of p53 ubiquitination in vivo. As indicated in FIG. 4A, a high level of ubiquitinated p53 was found in cells cotransfected with Mdm2 (lane 2); however, p53 ubiquitination was significantly abrogated by HAUSP expression (lane 3 vs. lane 2). In contrast, HAUSP had no effect on the levels of ubiquitinated p27 (data not shown). Notably, an unrelated human UBP family member (human USP11) (D'Andrea and Pellman, supra; Chung and Baek, supra; Wilkinson, K. D., supra), which is defective in p53-binding (data not shown), had no obvious effect on the levels of p53 ubiquitination (lane 5, FIG. 4A) or p53 stabilization (lane 5, FIG. 4B). Significantly, a HAUSP mutant with a short deletion at the core domain lost the ability to stabilize p53 (lane 4, FIG. 4B) or reduce the cellular levels of p53 ubiquitination (lane 4, FIG. 4A), indicating that stabilization of p53 by HAUSP requires its deubiquitinating enzymatic activity.

To further confirm the specific deubiquitination activity of HAUSP on p53, the inventors examined whether HAUSP can directly deubiquitinate p53 in a purified system. The HAUSP protein was expressed in bacteria, and purified to near homogeneity. The ubiquitinated form of p53 then was purified on the M2 affinity column, under high stringency conditions, from the cells transfected with a Flag-tagged p53 expression vector. The highly purified in vitro system was used in this assay in order to avoid possible contamination by either inhibitory factors (i.e., p14ARF) or any enzymes involving ubiquitination of p53. As shown in FIG. 4C, p53 was efficiently deubiquitinated upon incubation with purified recombinant HAUSP (lane 2). Thus, the foregoing results demonstrate that HAUSP can specifically deubiquitinate p53, both in vitro and in vivo.

Interestingly, a HAUSP point-mutant protein (HAUSP-cs), in which a highly conserved Cys residue at the core domain was replaced by Ser, retained its strong binding with p53 (FIG. 9); however, the mutant was functionally defective in deubiquitinating p53 in vitro (lane 3, FIG. 4C). Significantly, in contrast to the effect produced by the wild-type of HAUSP, expression of HAUSP-cs in the cells increased the level of p53 ubiquitination (lane 4 vs. 2, FIG. 5A), indicating that HAUSP-cs may function as a dominant-negative mutant by interfering with endogenous HAUSP-mediated deubiquitination of p53.

Figure 5:
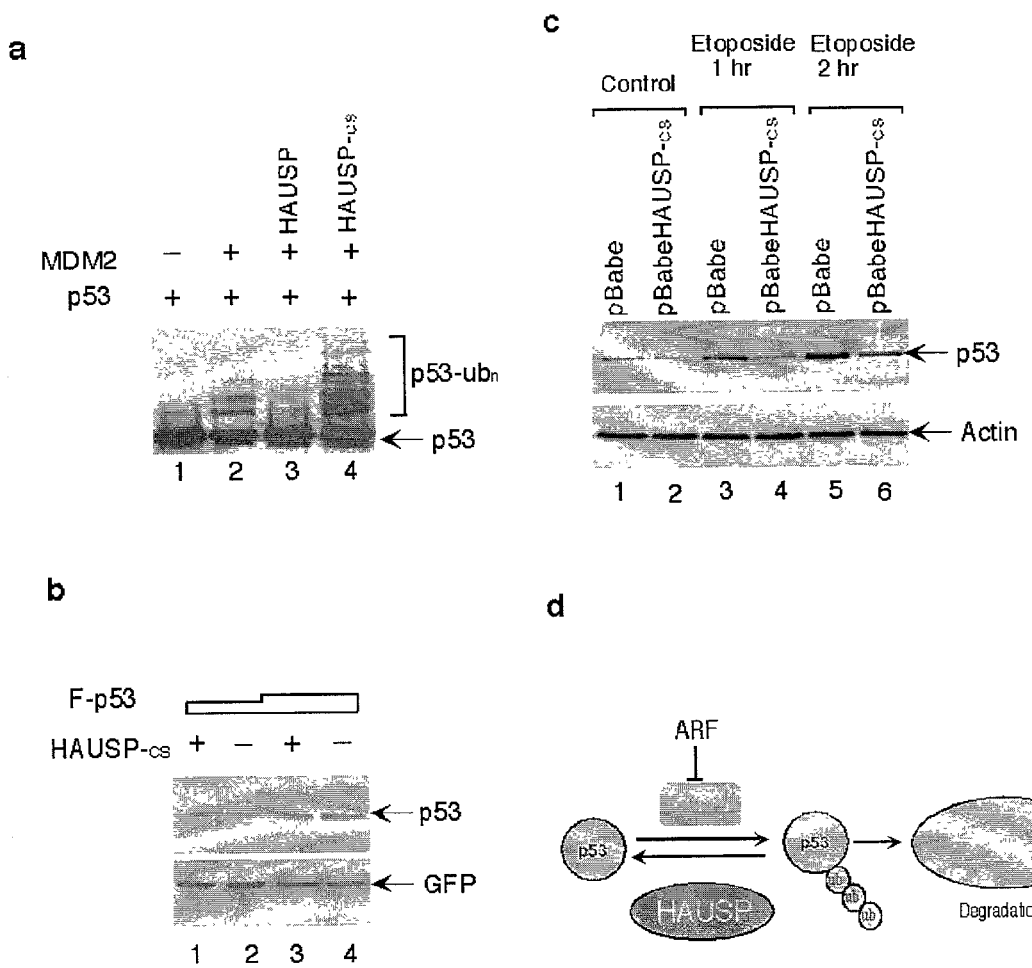

In order to corroborate these results, the inventors also tested whether HAUSP-cs expression affected the levels of p53 proteins in cells. As shown in FIG. 5B, co-expression of HAUSP-cs with p53 slightly, but significantly, decreased the levels of p53 proteins (lanes 1, 3 vs. lanes 2, 4). To demonstrate further that HAUSP regulates endogenous p53, the inventors introduced the point mutant (HAUSP-cs) into normal human cells. IMR-90 cells were infected with either a pBabe retrovirus empty vector or a pBabe retrovirus containing HAUSP-cs. As indicated in FIG. 5C, the levels of p53 proteins in the mock-infected cells were strongly induced by DNA damage (lanes 1, 3, 5). However, HAUSP-cs expression led to significant attenuation of p53 stabilization under both normal and DNA damage conditions (lanes 2, 4, 6). Taken together, these results suggest that HAUSP is critically involved in deubiquitination, as well as stabilization, of p53 under physiological conditions.

4. Discussion

The inventors' data suggest that HAUSP-mediated stabilization of p53 acts through its intrinsic deubiquitinating enzymatic activity. Deubiquitination, which removes the ubiquitin moiety from ubiquitin-modified proteins, is now recognized as an important regulatory step (D' Andrea and Pellman, supra; Chung and Baek, supra; Wilkinson, K.D., supra). The large number of UBPs also suggests that these proteins may bind to specific cellular proteins, and have substrate specificity (D' Andrea and Pellman, supra; Chung and Baek, supra; Wilkinson, K.D., supra). Although a growing number of UBP homologues have been identified in mammalian cells (D' Andrea and Pellman, supra; Chung and Baek, supra; Wilkinson, K.D., supra), thus far, none has been implicated in stabilizing specific substrates in vivo. HAUSP may represent the first example of a mammalian protein that can directly deubiquitinate and stabilize a specific cellular factor (p53). Accordingly, the inventors' findings have significant implications regarding the potential tumor-suppression function of HAUSP, and also predict that many UBP family proteins, like HAUSP, may interact with different substrates in vivo, for both deubiquitination and subsequent protein stabilization.

Previous studies have indicated that HAUSP interacts with the herpesvirus protein, Vmw110, and that a subset of the HAUSP proteins is localized with the PML nuclear body (Everett et al., supra). In addition, there is now growing evidence showing that ARF is dispensable for p53 activation induced by some types of oncogenic stress (Seavey et al, The E7 oncoprotein of human papillomavirus type 16 stabilizes p53 through a mechanism independent of p19 (ARF). *J. Virol.*, 73:7590-98, 1999; Tolbert et al., p19ARF is dispensable for oncogenic stress-induced p53-mediated apoptosis and tumor suppression in vivo. *Mol. Cell Biol.*, 22:370-77, 2002). Thus, these studies, taken together with the inventors' findings, further suggest potential regulation for the p53-HAUSP interaction in viral infection, DNA damage response, and other types of stress response.

Stabilization of p53 is critical for its effects on cell-growth repression and apoptosis. Numerous studies have proposed that stabilization of p53 in response to various types of stress may be achieved through inhibition of the Mdm2-p53 interaction and/or Mdm2-mediated ubiquitin ligase (Ashcroft and Vousden, supra; Freedman et al., supra; Sherr and Webber, supra). Stabilization of p53 is critical for its tumor-suppressor function (Ashcroft and Vousden, supra; Freedman et al., supra; Oren, M., supra; Prives and Hall, supra; Vogelstein et al., supra). The inventors' findings reveal that ubiquitination of p53 is a dynamic process in vivo, and that ubiquitinated p53 can be rescued from degradation by HAUSP through direct deubiquitination (FIG. 5D). It is very likely that changing the balance between Mdm2-mediated ubiquitination of p53 and HAUSP-mediated deubiquitination of p53 is the key for p53 stabilization in vivo.

EXAMPLE 2

To further evaluate in vivo interactions by co-immunoprecipitation analysis, p53-null cells (H1299) were transfected with p53 and a Flag-tagged HAUSP expression vector. As shown in FIG. 8A, p53 was readily immunoprecipitated from the cells cotransfected with both Flag-HAUSP and p53 (lane 4), but not from cells transfected with p53 alone (lane 2). By using the HAUSP-specific antibody, the inventors also examined the interaction between the endogenous p53 and HAUSP proteins. Western blot analysis showed that p53 was present in the a-HAUSP immunoprecipitates from cell extracts of human lung carcinoma cells (H460) which express wild-type p53 (lane 4, FIG. 8B), but not in the control immunoprecipitates obtained with the preimmune serum (lane 2, FIG. 8B). Interestingly, this interaction was shown to be much stronger in cells subjected to genotoxic stress (lane 3 vs. lane 4, FIG. 8B), whereas only a slight enhancement was detected in the cells treated with a proteasome inhibitor, LLNL (lane 5, FIG. 8B). Furthermore, enhancement of the p53-HAUSP interaction was observed as early as 2-4 h after DNA damage (FIG. 7C), strongly suggesting a critical role for HAUSP in regulating p53 stability during the DNA-damage response. Thus, in contrast to abrogation of the Mdm2-p53 interaction by DNA damage (Shieh et al., supra) these results indicate that p53 interacts with HAUSP in vivo, and that this interaction is enhanced in the cells after DNA damage, consistent with the suggestion that endogenous HAUSP plays an important role in p53 stabilization.

While the foregoing invention has been described in some detail for purposes of clarity and understanding, it will be appreciated by one skilled in the art, from a reading of the disclosure, that various changes in form and detail can be made without departing from the true scope of the invention in the appended claims.

What is claimed is:

1. A method for determining whether a subject has a neoplasia associated with a defect in a p53 pathway, the method comprising detecting Herpes-Associated Ubiquitin Specific Protease (HAUSP)-p53 protein complex in a sample from the subject, wherein detection of HAUSP-p53 protein complex at a level elevated above normal in the subject is diagnostic of the neoplasia.

2. The method of claim 1, wherein the neoplasia is a carcinoma, a lymphocytic leukemia, a myeloid leukemia, a malignant lymphoma, a malignant melanoma, a myeloproliferative disease, a sarcoma, or a mixed type of neoplasia.

3. The method of claim 1, wherein the sample is assayed using an antibody, or an antigen-binding fragment thereof, reactive with Herpes-Associated Ubiquitin Specific Protease (HAUSP).

4. The method of claim 3, wherein the antibody, or an antigen-binding fragment thereof, is labeled with a detectable marker.

5. The method of claim 1, wherein the defect in a p53 pathway comprises a disruption in a p53 gene.

6. The method of claim 1, wherein the defect in a p53 pathway comprises an increase in the rate of degradation of p53 protein.

* * * * *

UNITED STATES PATENT AND TRADEMARK OFFICE
CERTIFICATE OF CORRECTION

PATENT NO. : 7,425,538 B2  Page 1 of 1
APPLICATION NO. : 10/113732
DATED : September 16, 2008
INVENTOR(S) : Wei Gu et al.

It is certified that error appears in the above-identified patent and that said Letters Patent is hereby corrected as shown below:

At column 1, line 7, please delete "RO1-CAS5533" and insert --RO1-CA085533--.

Signed and Sealed this

Fourteenth Day of July, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,425,538 B2
APPLICATION NO. : 10/113732
DATED : September 16, 2008
INVENTOR(S) : Wei Gu et al.

Page 1 of 1

It is certified that error appears in the above-identified patent and that said Letters Patent is hereby corrected as shown below:

In the Specification

On column 1, lines 4-8, please amend as follows:

-- STATEMENT OF GOVERNMENT INTEREST

This invention was made with government support under NIH Grant No. ~~R01 CAS5533~~ CA085533. As such, the ~~United States~~ government has certain rights in the invention. --

Signed and Sealed this
First Day of October, 2013

Teresa Stanek Rea
*Deputy Director of the United States Patent and Trademark Office*

SEQUENCE LISTING

```
<160> NUMBER OF SEQ ID NOS: 7

<210> SEQ ID NO 1
<211> LENGTH: 13
<212> TYPE: PRT
<213> ORGANISM: Homo sapiens

<400> SEQUENCE: 1

Tyr Asp Ala Gly Glu His Gly Leu Gln Glu Ala Glu Lys
1               5                   10

<210> SEQ ID NO 2
<211> LENGTH: 13
<212> TYPE: PRT
<213> ORGANISM: Homo sapiens

<400> SEQUENCE: 2

Asp Phe Glu Pro Gln Pro Gly Asn Met Ser His Pro Arg
1               5                   10
```

```
<210> SEQ ID NO 3
<211> LENGTH: 8
<212> TYPE: PRT
<213> ORGANISM: Homo sapiens

<400> SEQUENCE: 3

Lys Leu Tyr Tyr Gln Gln Leu Lys
1               5

<210> SEQ ID NO 4
<211> LENGTH: 12
<212> TYPE: PRT
<213> ORGANISM: Homo sapiens

<400> SEQUENCE: 4

Phe Met Tyr Asp Pro Gln Thr Asp Gln Asn Ile Lys
1               5                   10

<210> SEQ ID NO 5
<211> LENGTH: 10
<212> TYPE: PRT
<213> ORGANISM: Homo sapiens

<400> SEQUENCE: 5

Ile Gln Asp Tyr Asp Val Ser Leu Asp Lys
1               5                   10

<210> SEQ ID NO 6
<211> LENGTH: 1102
<212> TYPE: PRT
<213> ORGANISM: Homo sapiens

<400> SEQUENCE: 6
```

Met Asn His Gln Gln Gln Gln Gln Gln Lys Ala Gly Glu Gln Gln
1               5                   10                  15

Leu Ser Glu Pro Glu Asp Met Glu Met Glu Ala Gly Asp Thr Asp Asp
            20                  25                  30

Pro Pro Arg Ile Thr Gln Asn Pro Val Ile Asn Gly Asn Val Ala Leu
        35                  40                  45

Ser Asp Gly His Asn Thr Ala Glu Glu Asp Met Glu Asp Asp Thr Ser
    50                  55                  60

Trp Arg Ser Glu Ala Thr Phe Gln Phe Thr Val Glu Arg Phe Ser Arg
65                  70                  75                  80

Leu Ser Glu Ser Val Leu Ser Pro Pro Cys Phe Val Arg Asn Leu Pro
                85                  90                  95

Trp Lys Ile Met Val Met Pro Arg Phe Tyr Pro Asp Arg Pro His Gln
            100                 105                 110

Lys Ser Val Gly Phe Phe Leu Gln Cys Asn Ala Glu Ser Asp Ser Thr
        115                 120                 125

Ser Trp Ser Cys His Ala Gln Ala Val Leu Lys Ile Ile Asn Tyr Arg
    130                 135                 140

Asp Asp Glu Lys Ser Phe Ser Arg Arg Ile Ser His Leu Phe His
145                 150                 155                 160

Lys Glu Asn Asp Trp Gly Phe Ser Asn Phe Met Ala Trp Ser Glu Val
                165                 170                 175

Thr Asp Pro Glu Lys Gly Phe Ile Asp Asp Lys Val Thr Phe Glu
            180                 185                 190

Val Phe Val Gln Ala Asp Ala Pro His Gly Val Ala Trp Asp Ser Lys
        195                 200                 205

-continued

```
Lys His Thr Gly Tyr Val Gly Leu Lys Asn Gln Gly Ala Thr Cys Tyr
210                 215                 220
Met Asn Ser Leu Leu Gln Thr Leu Phe Phe Thr Asn Gln Leu Arg Lys
225                 230                 235                 240
Ala Val Tyr Met Met Pro Thr Glu Gly Asp Asp Ser Ser Lys Ser Val
                245                 250                 255
Pro Leu Ala Leu Gln Arg Val Phe Tyr Glu Leu Gln His Ser Asp Lys
                260                 265                 270
Pro Val Gly Thr Lys Lys Leu Thr Lys Ser Phe Gly Trp Glu Thr Leu
                275                 280                 285
Asp Ser Phe Met Gln His Asp Val Gln Glu Leu Cys Arg Val Leu Leu
        290                 295                 300
Asp Asn Val Glu Asn Lys Met Lys Gly Thr Cys Val Glu Gly Thr Ile
305                 310                 315                 320
Pro Lys Leu Phe Arg Gly Lys Met Val Ser Tyr Ile Gln Cys Lys Glu
                325                 330                 335
Val Asp Tyr Arg Ser Asp Arg Arg Glu Asp Tyr Tyr Asp Ile Gln Leu
                340                 345                 350
Ser Ile Lys Gly Lys Lys Asn Ile Phe Glu Ser Phe Val Asp Tyr Val
                355                 360                 365
Ala Val Glu Gln Leu Asp Gly Asp Asn Lys Tyr Asp Ala Gly Glu His
            370                 375                 380
Gly Leu Gln Glu Ala Glu Lys Gly Val Lys Phe Leu Thr Leu Pro Pro
385                 390                 395                 400
Val Leu His Leu Gln Leu Met Arg Phe Met Tyr Asp Pro Gln Thr Asp
                405                 410                 415
Gln Asn Ile Lys Ile Asn Asp Arg Phe Glu Phe Pro Gly Gln Leu Pro
                420                 425                 430
Leu Asp Glu Phe Leu Gln Lys Thr Asp Pro Lys Asp Pro Ala Asn Tyr
            435                 440                 445
Ile Leu His Ala Val Leu Val His Ser Gly Asp Asn His Gly Gly His
            450                 455                 460
Tyr Val Val Tyr Leu Asn Pro Lys Gly Asp Gly Lys Trp Cys Lys Phe
465                 470                 475                 480
Asp Asp Asp Val Val Ser Arg Cys Thr Lys Glu Glu Ala Ile Glu His
                485                 490                 495
Asn Tyr Gly Gly His Asp Asp Asp Leu Ser Val Arg His Cys Thr Asn
                500                 505                 510
Ala Tyr Met Leu Val Tyr Ile Arg Glu Ser Lys Leu Ser Glu Val Leu
            515                 520                 525
Gln Ala Val Thr Asp His Asp Ile Pro Gln Gln Leu Val Glu Arg Leu
530                 535                 540
Gln Glu Glu Lys Arg Ile Glu Ala Gln Lys Arg Lys Glu Arg Gln Glu
545                 550                 555                 560
Ala His Leu Tyr Met Gln Val Gln Ile Val Ala Glu Asp Gln Phe Cys
                565                 570                 575
Gly His Gln Gly Asn Asp Met Tyr Asp Glu Glu Lys Val Lys Tyr Thr
            580                 585                 590
Val Phe Lys Val Leu Lys Asn Ser Ser Leu Ala Glu Phe Val Gln Ser
            595                 600                 605
Leu Ser Gln Thr Met Gly Phe Pro Gln Asp Gln Ile Arg Leu Trp Pro
        610                 615                 620
Met Gln Ala Arg Ser Asn Gly Thr Lys Arg Pro Ala Met Leu Asp Asn
```

```
                625                 630                 635                 640
Glu Ala Asp Gly Asn Lys Thr Met Ile Glu Leu Ser Asp Asn Glu Asn
                    645                 650                 655
Pro Trp Thr Ile Phe Leu Glu Thr Val Asp Pro Glu Leu Ala Ala Ser
                    660                 665                 670
Gly Ala Thr Leu Pro Lys Phe Asp Lys Asp His Asp Val Met Leu Phe
                    675                 680                 685
Leu Lys Met Tyr Asp Pro Lys Thr Arg Ser Leu Asn Tyr Cys Gly His
    690                 695                 700
Ile Tyr Thr Pro Ile Ser Cys Lys Ile Arg Asp Leu Leu Pro Val Met
705                 710                 715                 720
Cys Asp Arg Ala Gly Phe Ile Gln Asp Thr Ser Leu Ile Leu Tyr Glu
                    725                 730                 735
Glu Val Lys Pro Asn Leu Thr Glu Arg Ile Gln Asp Tyr Asp Val Ser
                    740                 745                 750
Leu Asp Lys Ala Leu Asp Glu Leu Met Asp Gly Asp Ile Ile Val Phe
                    755                 760                 765
Gln Lys Asp Asp Pro Glu Asn Asp Asn Ser Glu Leu Pro Thr Ala Lys
    770                 775                 780
Glu Tyr Phe Arg Asp Leu Tyr His Arg Val Asp Val Ile Phe Cys Asp
785                 790                 795                 800
Lys Thr Ile Pro Asn Asp Pro Gly Phe Val Val Thr Leu Ser Asn Arg
                    805                 810                 815
Met Asn Tyr Phe Gln Val Ala Lys Thr Val Ala Gln Arg Leu Asn Thr
                    820                 825                 830
Asp Pro Met Leu Leu Gln Phe Phe Lys Ser Gln Gly Tyr Arg Asp Gly
                    835                 840                 845
Pro Gly Asn Pro Leu Arg His Asn Tyr Glu Gly Thr Leu Arg Asp Leu
    850                 855                 860
Leu Gln Phe Phe Lys Pro Arg Gln Pro Lys Lys Leu Tyr Tyr Gln Gln
865                 870                 875                 880
Leu Lys Met Lys Ile Thr Asp Phe Glu Asn Arg Arg Ser Phe Lys Cys
                    885                 890                 895
Ile Trp Leu Asn Ser Gln Phe Arg Glu Glu Ile Thr Leu Tyr Pro
                    900                 905                 910
Asp Lys His Gly Cys Val Arg Asp Leu Leu Glu Glu Cys Lys Lys Ala
                    915                 920                 925
Val Glu Leu Gly Glu Lys Ala Ser Gly Lys Leu Arg Leu Leu Glu Ile
    930                 935                 940
Val Ser Tyr Lys Ile Ile Gly Val His Gln Glu Asp Glu Leu Leu Glu
945                 950                 955                 960
Cys Leu Ser Pro Ala Thr Ser Arg Thr Phe Arg Ile Glu Glu Ile Pro
                    965                 970                 975
Leu Asp Gln Val Asp Ile Asp Lys Glu Asn Glu Met Leu Val Thr Val
                    980                 985                 990
Ala His Phe His Lys Glu Val Phe Gly Thr Phe Gly Ile Pro Phe Leu
                    995                 1000                1005
Leu Arg Ile His Gln Gly Glu His Phe Arg Glu Val Met Lys Arg
    1010                1015                1020
Ile Gln Ser Leu Leu Asp Ile Gln Glu Lys Glu Phe Glu Lys Phe
    1025                1030                1035
Lys Phe Ala Ile Val Met Thr Gly Arg His Gln Tyr Ile Asn Glu
    1040                1045                1050
```

Asp Glu Tyr Glu Val Asn Leu Lys Asp Phe Glu Pro Gln Pro Gly
        1055                1060                1065

Asn Met Ser His Pro Arg Pro Trp Leu Gly Leu Asp His Phe Asn
    1070                1075                1080

Lys Ala Pro Lys Arg Ser Arg Tyr Thr Tyr Leu Glu Lys Ala Ile
    1085                1090                1095

Lys Ile His Asn
    1100

<210> SEQ ID NO 7
<211> LENGTH: 4022
<212> TYPE: DNA
<213> ORGANISM: Homo sapiens

<400> SEQUENCE: 7

| | | | | | |
|---|---|---|---|---|---|
| gtacgtgcgc | gtctccctgc | cgccgccgcc | gcccgccgcg | ggccgccccg | gggccgccgt | 60 |
| cgccgacgac | gcgcgggagg | aggaggagga | ggccgccccg | ccgccgccgc | cgccgccgcc | 120 |
| gccccggctc | gccgccgccc | gcccgccggg | ctcgcagccc | cggcccccgg | ccgcaggcga | 180 |
| ggcccaggcc | gcggccgaca | tgaaccacca | gcagcagcag | cagcagcaga | aagcgggcga | 240 |
| gcagcagttg | agcgagcccg | aggacatgga | gatggaagcg | ggagatacag | atgacccacc | 300 |
| aagaattact | cagaaccctg | tgatcaatgg | gaatgtggcc | ctgagtgatg | acacaacac | 360 |
| cgcggaggag | gacatggagg | atgacaccag | ttggcgctcc | gaggcaacct | ttcagttcac | 420 |
| tgtggagcgc | ttcagcagac | tgagtgagtc | ggtccttagc | cctccgtgtt | ttgtgcgaaa | 480 |
| tctgccatgg | aagattatgg | tgatgccacg | cttttatcca | gacagaccac | accaaaaaag | 540 |
| cgtaggattc | tttctccagt | gcaatgctga | atctgattcc | acgtcatggt | cttgccatgc | 600 |
| acaagcagtg | ctgaagataa | taaattacag | agatgatgaa | agtcgttca | gtcgtcgtat | 660 |
| tagtcatttg | ttcttccata | agaaaatga | ttggggattt | tccaattta | tggcctggag | 720 |
| tgaagtgacc | gatcctgaga | aggatttat | agatgatgac | aaagttacct | ttgaagtctt | 780 |
| tgtacaggcg | gatgctcccc | atggagttgc | gtgggattca | agaagcaca | caggctacgt | 840 |
| cggcttaaag | aatcagggag | cgacttgtta | catgaacagc | ctgctacaga | cgttattttt | 900 |
| cacgaatcag | ctacgaaagg | ctgtgtacat | gatgccaacc | gagggggatg | attcgtctaa | 960 |
| aagcgtccct | ttagcattac | aaagagtgtt | ctatgaatta | cagcatagtg | ataaacctgt | 1020 |
| aggaacaaaa | aagttaacaa | agtcatttgg | gtgggaaact | ttagatagct | tcatgcaaca | 1080 |
| tgatgttcag | gagctttgtc | gagtgttgct | cgataatgtg | gaaaataaga | tgaaaggcac | 1140 |
| ctgtgtagag | ggcaccatac | ccaaattatt | ccgcggcaaa | atggtgtcct | atatccagtg | 1200 |
| taaagaagta | gactatcggt | ctgatagaag | agaagattat | tatgatatcc | agctaagtat | 1260 |
| caaaggaaaa | aaaatatat | ttgaatcatt | tgtggattat | gtggcagtag | aacagctcga | 1320 |
| tggggacaat | aaatacgacg | ctggggaaca | tggcttacag | gaagcagaga | aggtgtgaa | 1380 |
| attcctaaca | ttgccaccag | tgttacatct | acaactgatg | agatttatgt | atgaccctca | 1440 |
| gacggaccaa | aatatcaaga | tcaatgatag | gtttgaattc | ccagagcagt | taccacttga | 1500 |
| tgaattttg | caaaaaacag | atcctaagga | ccctgcaaat | tatattcttc | atgcagtcct | 1560 |
| ggttcatagt | ggagataatc | atggtggaca | ttatgtggtt | tatctaaacc | ccaaggggga | 1620 |
| tggcaaatgg | tgtaaatttg | atgacgacgt | ggtgtcaagg | tgtactaaag | aggaagcaat | 1680 |
| tgagcacaat | tatgggggtc | acgatgacga | cctgtctgtt | cgacactgca | ctaatgctta | 1740 |

```
catgttagtc tacatcaggg aatcaaaact gagtgaagtt ttacaggcgg tcaccgacca   1800
tgatattcct cagcagttgg tggagcgatt acaagaagag aaaaggatcg aggctcagaa   1860
gcggaaggag cggcaggaag cccatctcta tatgcaagtg cagatagtcg cagaggacca   1920
gttttgtggc caccaaggga atgacatgta cgatgaagaa aaagtgaaat acactgtgtt   1980
caaagtattg aagaactcct cgcttgctga gtttgttcag agcctctctc agaccatggg   2040
atttccacaa gatcaaattc gattgtggcc catgcaagca aggagtaatg gaacaaaacg   2100
accagcaatg ttagataatg aagccgacgg caataaaaca atgattgagc tcagtgataa   2160
tgaaaaccct tggacaatat tcctggaaac agttgatccc gagctggctg ctagtggagc   2220
gaccttaccc aagtttgata agatcatga tgtaatgtta tttttgaaga tgtatgatcc   2280
caaaacgcgg agcttgaatt actgtgggca tatctcacaca ccaatatcct gtaaaatacg   2340
tgacttgctc ccagttatgt gtgacagagc aggatttatt caagatacta gccttatcct   2400
ctatgaggaa gttaaaccga atttaacaga gagaattcag gactatgacg tgtctcttga   2460
taaagccctt gatgaactaa tggatggtga catcatagta tttcagaagg atgaccctga   2520
aaatgataac agtgaattac ccaccgcaaa ggagtatttc cgagatctct accaccgcgt   2580
tgatgtcatt ttctgtgata aaacaatccc taatgatcct ggatttgtgg ttacgttatc   2640
aaatagaatg aattattttc aggttgcaaa gacagttgca cagaggctca acacagatcc   2700
aatgttgctg cagttttca gtctcaagg ttatagggat ggcccaggta atcctcttag   2760
acataattat gaaggtactt taagagatct tctacagttc ttcaagccta gacaacctaa   2820
gaaactttac tatcagcagc ttaagatgaa aatcacagac tttgagaaca ggcgaagttt   2880
taaatgtata tggttaaaca gccaatttag ggaagaggaa ataacactat atccagacaa   2940
gcatgggtgt gtccgggacc tgttagaaga atgtaaaaag gccgtggagc ttggggagaa   3000
agcatcaggg aaacttaggc tgctagaaat tgtaagctac aaaatcattg gtgttcatca   3060
agaagatgaa ctattagaat gtttatctcc tgcaacgagc cggacgtttc gaatagagga   3120 aatcccttg gaccaggtgg acatagacaa agagaatgag atgcttgtca cagtggcgca   3180
tttccacaaa gaggtcttcg gaacgttcgg aatcccgttt ttgctgagga tacaccaggg   3240
cgagcatttt cgagaagtga tgaagcgaat ccagagcctg ctggacatcc aggagaagga   3300
gtttgagaag tttaaatttg caattgtaat gacgggccga caccagtaca taaatgaaga   3360
cgagtatgaa gtaaatttga aagactttga gccacagccc ggtaatatgt ctcatcctcg   3420
gccttggcta gggctcgacc acttcaacaa agccccaaag aggagtcgct acacttacct   3480
tgaaaaggcc attaaaatcc ataactgatt tccaagctgg tgtgttcaag gcgaggacgg   3540
tgtgtgggtg gccccttaac agcctagaac tttggtgcac gtgccctcta gccgaagtct   3600
tcagcaagag gattcgctgc tggtgttaat tttattttat tgaggctgtt cagtttggct   3660
tctctgtatc tattgactgc ccttttgag caaaatgaag atgttttttat aaagcttgga   3720 tgccaatgag agttatttta tggtaaccac agtgcaaggc aactgtcagc gcaatggggg   3780
agaagaggtt agtggatcgg gggtccctgg ctcaaggtct ctgggctgtc cctagtgggc   3840
acgagtggct cggctgcctt cctggggtcc cgtgcaccag ccctgcagct agcaagtctt   3900
gtgtttaggc tcgtctgacc tatttccttc agttatactt tcaatgacct tttgtgcatc   3960
tgttaaggca aaacagagaa actcacaacc taataaatag cgctcttccc ttcaaaaaaa   4020
aa                                                                 4022
```